United States Patent [19]

Kopecek et al.

[11] Patent Number: 5,037,883
[45] Date of Patent: Aug. 6, 1991

[54] SYNTHETIC POLYMERIC DRUGS

[75] Inventors: Jindrich Kopecek; Pavla Rejmanova; Jiri Strohalm; Karel Ulbrich; Blanka Rihova; Vladimir Chytry, all of Prague, Czechoslovakia; John B. Lloyd; Ruth Duncan, both of Keele, England

[73] Assignees: Ceskoslovenska Akademie Ved, Praha, Czechoslovakia; Carlton Medical Products Limited, London, England

[21] Appl. No.: 438,352

[22] Filed: Nov. 17, 1989

[30] Foreign Application Priority Data

Jan. 4, 1985 [GB] United Kingdom ................ 8500209

[51] Int. Cl.$^5$ .................... C08G 63/48; C08G 63/91
[52] U.S. Cl. ................... 525/54.1; 526/238.1; 526/238.2; 530/811; 530/812; 530/815; 530/816
[58] Field of Search ............. 525/54.1; 526/238.1, 526/238.2; 530/350, 386, 405, 811, 812, 815, 816; 435/181; 436/532

[56] References Cited

U.S. PATENT DOCUMENTS 3,522,196 7/1970 Dorier et al. ................ 521/187
3,957,700 5/1976 Ferriday et al. .............. 521/187
4,007,142 2/1977 Clarke et al. ................. 521/187

OTHER PUBLICATIONS

Ringsdorf et al., "Bis(2-Chloroethyl)Amine Bound to Copolymers of N-(2-Hydroxypropyl)Methacrylamide and Methacryloylated Oligopeptides via Biodegradable Bonds", Makromol. Chem., 188, 257-264 (1987).
Kopecek, Biomaterials, 5, 1984, 19-26, "Controlled Biodegradability of Polymers-A Key to Drug Delivery Systems".
Kopecek, Recent Advances in Drug Delivery Systems, Ed. Anderson et al., Plenum Press, New York (1984), "Synthesis of Tailor-Made Soluble Polymeric Drug Carriers", pp. 41-62.
Kopecek, IUPAC Macromolecules, Ed. Benoit et al., Pergamon Press, New York (1982), "Biodegradation of Polymers for Biomedical Use", pp. 305-319.

Primary Examiner—Nathan M. Nutter
Attorney, Agent, or Firm—Marshall, O'Toole, Gerstein, Murray & Bicknell

[57] ABSTRACT

A polymeric drug comprising an inert synthetic polymeric carrier combined through aminoacid or peptide spacers with a bioactive molecule, a targeting moiety, and an optional cross-linkage, comprises:

(a) 5.0 to 99.7 mol % of units derived from N-(2-hydroxypropyl)methacrylamide,
(b) 0.2 to 20.0 mol % of units derived from an N-methylacrylcylated peptide, the peptide groups being bound to a bioactive moiety,
(c) 0.1 to 94.8 mol % of units derived from N-methacrylamide, N-methacrylic acid or an N-methacrylolated aminoacid or peptide, to which are bound a determinant capable of interacting with specific receptors on cell surfaces,
(d) optionally, 0 to 5 mol % of units derived from an N-methacryloylated peptide, the peptide groups being bound to a linking group which is similarly to a similar peptide group attached to another polymer chain, and
(e) optionally, as a bioassay label, 0 to 2 mol % units derived from N-methyacryloylated tyrosinamide.

19 Claims, 6 Drawing Sheets

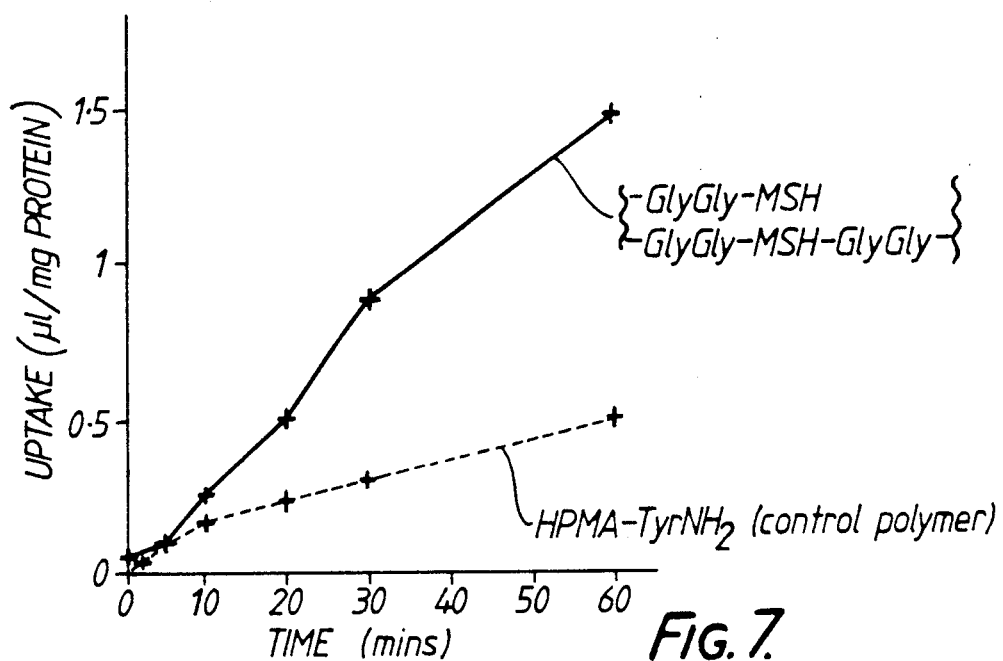
FIG. 7. RATE OF IN VITRO UPTAKE OF HPMA-MSH COPOLYMER BY CLONE M3 MELANOMA CELLS
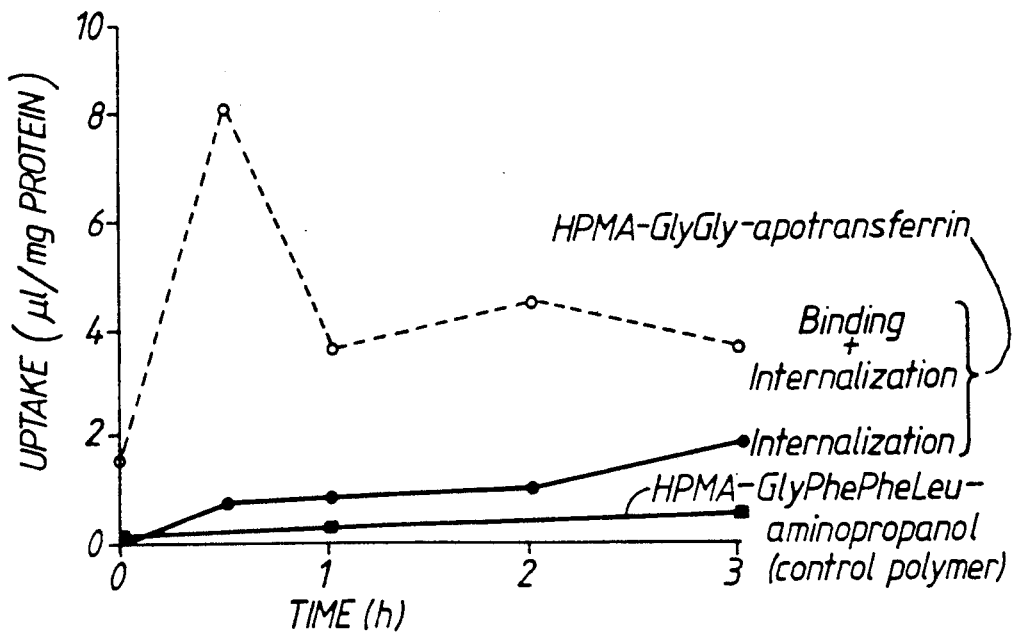
FIG. 8. RATE OF IN VITRO UPTAKE OF HPMA-apotransferrin COPOLYMER BY HUMAN FIBROBLASTS IN VITRO UPTAKE OF HPMA-galactose COPOLYMER BY HUMAN HEPATOMA CELLS AS FUNCTION OF mol % GALACTOSE IN COPOLYMER EFFECT OF HPMA-daunomycin COPOLYMERS ON ACTIVITY OF L1210 MOUSE LEUKAEMIA IN VITRO

SYNTHETIC POLYMERIC DRUGS

This is a continuation of application Ser. No. 06/816,138, filed Jan. 3, 1986, now abandoned.

The present invention is concerned with polymeric drugs comprising an inert synthetic polymeric carrier combined through a biodegradable spacer with a low molecular weight bioactive molecule and with the synthesis thereof.

Many of the low molecular weight drugs used in chemotherapy rapidly enter all types of cell by random diffusion through the cell membrane. This lack of selectivity decreases their availability at the desired target tissue and sometimes causes undesirable side effects. Cellular uptake is rapid so that the therapeutic effect is not extended over a period of time. Furthermore, glomerular filtration can rapidly remove the drugs from the bloodstream.

The covalent attachment of low molecular weight bioactive molecules to soluble polymeric carriers prevents both glomerular filtration and cellular absorption by simple diffusion. Uptake is restricted to cells capable of a substrate selective mechanism known as pinocytosis, in which a region of the limiting membrane of the cell engulfs the macromolecule and is then detached inwards to form a free intracellular vesicle containing the captured material.

This difference in uptake mechanisms affords a potential method for directing drugs specifically to those cells where their therapeutic effect is required.

A further difference lies in the subsequent fates of the two types of molecule. Small molecules which enter by diffusion tend to find their way to all parts of the cell, but macromolecules, following pinocytosis, are transported in their intracellular vesicles directly to the lysosomal compartment of the cell where an array of hydrolytic enzymes is available.

The pinocytic uptake of a polymeric drug in which the drug-carrier linkage is susceptible to lysosomal hydrolysis therefore affords a mechanism for the controlled intracellular release of a bioactive molecule leading to its appearance within the cytoplasm of the target cell. The theoretical considerations involved in the design of such a drug system have recently been reviewed in an article by J. Kopecek entitled "Synthesis of tailormade soluble polymeric carriers" in "Recent Advances in Drug Delivery Systems" (Plenum Press, 1984).

In order to design such a system, two criteria must be satisfied. Firstly, a drug-carrier linkage must be devised which undergoes controlled lysosomal hydrolysis, but is capable of withstanding the action of enzymes in the bloodstream. Secondly, the drug delivery system must be able to achieve specific uptake at those target cells where the therapeutic effect is required, with minimal uptake by other cells.

Although the process of pinocytosis affords a degree of selectivity towards macromolecules, a selectivity which can be optimised by varying the molecular weight, greater target selectivity can be achieved by the incorporation within the macromolecule of a specific "targeting moiety". Cells possess specific receptors and cell antigens on their surfaces which "recognise" and interact with certain types of molecular entities known as specific determinants. High cell specificity can be achieved by the incorporation in the polymeric drug of a determinant which is recognised by the type of cells in which the therapeutic effect is required.

Thus, a drug delivery system which would allow specific targeting followed by intracellular drug release requires the following features:

(a) an inert polymeric carrier, which is preferably susceptible to lysosomal hydrolysis to facilitate elimination of the polymer from the body, (b) a degradable drug-carrier linkage which is resistant to extracellular hydrolysis, but which is subject to controlled lysosomal hydrolysis, and (c) a specific targeting moiety.

Such a molecule may be represented by the following schematic representation:

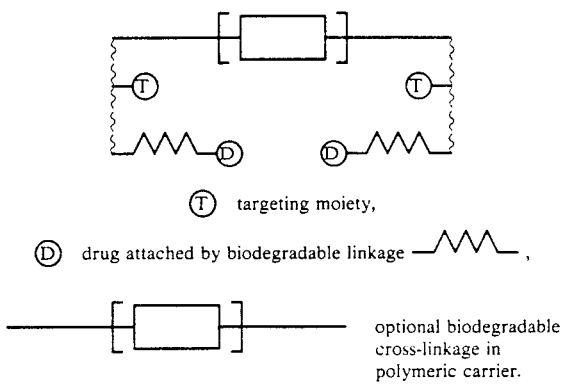

Ⓣ targeting moiety,

Ⓓ drug attached by biodegradable linkage —⋀⋀⋀— ,

———[ ☐ ]———  optional biodegradable cross-linkage in polymeric carrier.

Although natural macromolecules have been used as carriers, synthetic polymers offer the advantages that the molecular weight can be more readily adjusted for optimum cell selectivity and, unlike many natural macromolecules, they are not immunogenic. They also lend themselves more readily to commercial production.

Synthetic polymers based on N-(2-hydroxypropyl)-methacrylamide (HPMA) have been proposed as potential drug carriers, see U.S. Pat. Nos. 4,062,831 and 4,097,470; such polymers are soluble in aqueous media and have good biocompatibility. Furthermore, by the incorporation of p-nitrophenylesters of N-methacryloyl oligopeptides they can be combined with many drugs which contain a primary amino group. The polymeric chains may be cross-linked to a level below the gel point in order to achieve the optimum molecular weight and to provide, by the use of biodegradable cross-linkages, a means of degrading the polymer to facilitate elimination from the body.

Since lysosomal enzymes include a number of proteinases with the ability to hydrolyse peptide linkages, direct linkage of the bioactive molecule to the polymer chain by an amide bond would appear to have the potential for lysosomal hydrolysis. In practice, this is not found to be the case. However, peptide "spacers" interposed between the drug and the carrier have been found to undergo degradation by lysosomal enzymes within a broad range of rates. The bond actually cleaved is usually that between the drug and the neighbouring aminoacid, although this is not always the case. The rate of hydrolysis, that is the rate of drug release, is found to depend greatly on the number and the nature of the aminoacid residues in the peptide spacer. Spacers of less than three aminoacids were not generally susceptible to lysosomal hydrolysis. Peptide spacers designed to match the known substrate specificity of thiol-proteinases, known to be present in lysosomes, are particularly effectively cleaved.

It has been demonstrated that the modification of glycoproteins to give oligosaccharide side-chains which terminate in galactose leads to a dramatic increase in the deposition of the glycoproteins in the parenchymal cells of the liver. The galactose moiety acts as a specific determinant interacting with receptors localised on the plasma membrane of the liver cells. This offers a potential mechanism for the targeting of drugs to hepatoma, a particularly difficult cancer to treat. Furthermore, galactosamine bound to HPMA copolymers by an amide bond gives a similar result, indicating that the receptors on hepatocyte membranes recognise the galactose moiety not only in glycosides, but also when present as N-acyl galactosamine. A number of other recognition systems are known, for example, the N-acetylglucosamine/mannose recognition system of Kupffer cells and macrophages and the phosphohexose recognition system of fibroblasts.

Another possible targeting mechanism is to bind the polymeric drug to an antibody which is recognised specifically by those cells which have the appropriate antigenic receptors. Drug molecules have been bound directly to immunoglobulins, but this can lead to loss of drug activity, loss of antibody activity and/or solubility of the conjugate.

A further targeting mechanism is to include a protein or a hormone, for example transferrin and melanocyte-stimulating hormone, which will bind specifically to the target cell type.

While the desirability of synthesising targeted polymeric drugs with hydrolysable peptide spacers has been referred to in the prior art (see the Kopecek article above), the identification of peptide spacers which are capable of controlled intracellular drug release at a satisfactory rate and the identification of linking group/determinant combinations which give good targeting to the desired cell receptors, have both eluded researchers.

As discussed earlier, the rate of lysosomal hydrolysis of a peptide spacer is dependent on both the number and the nature of the aminoacid residues. This is a reflection of both steric and structural factors. Thus the rate of terminal hydrolysis of a spacer containing 2 to 4 aminoacid residues is generally dependent on the number of residues present, an effect attributed to steric interaction between the polymer chain and the enzyme.

For a given length of peptide, the rate of hydrolysis is dependent on the nature (and sequence) of the aminoacid residues. This dependency arises from the substrate specific nature of the lysosomal enzymes responsible for cleavage of the peptide spacer. The region of the enzyme where interaction with the substrate takes place is known as the "active site" of the enzyme. The active site performs the dual role of binding the substrate while catalysing the reaction, for example cleavage. Studies of the structures of the complexes of proteolytic enzymes with peptides indicate that the active site of these enzymes is relatively large and binds to several aminoacid residues in the peptide.

Thus the degradability of a particular bond in a peptide chain depends not only on the nature of the structure near the cleaved bond, but also on the nature of the aminoacid residues which are relatively remote from the cleaved bond, but play an important part in holding the enzyme in position during hydrolysis. So far the detailed structures of the active sites of lysosomal enzymes have not been determined and this has proved to be an obstacle to the preparation of peptide spacers which undergo lysosomal hydrolysis at a suitable rate for use in polymer drugs.

FIG. 7 is a graphical depiction of the rate of in vitro uptake of HPMA-MSH copolymer by Clone M3 melanoma cells, as described in Example 29.

FIG. 8 is a graphical depiction of the rate of in vitro uptake of HPMA-apotransferrin copolymer by human fibroblasts, as described in Example 30.

Figure 1:
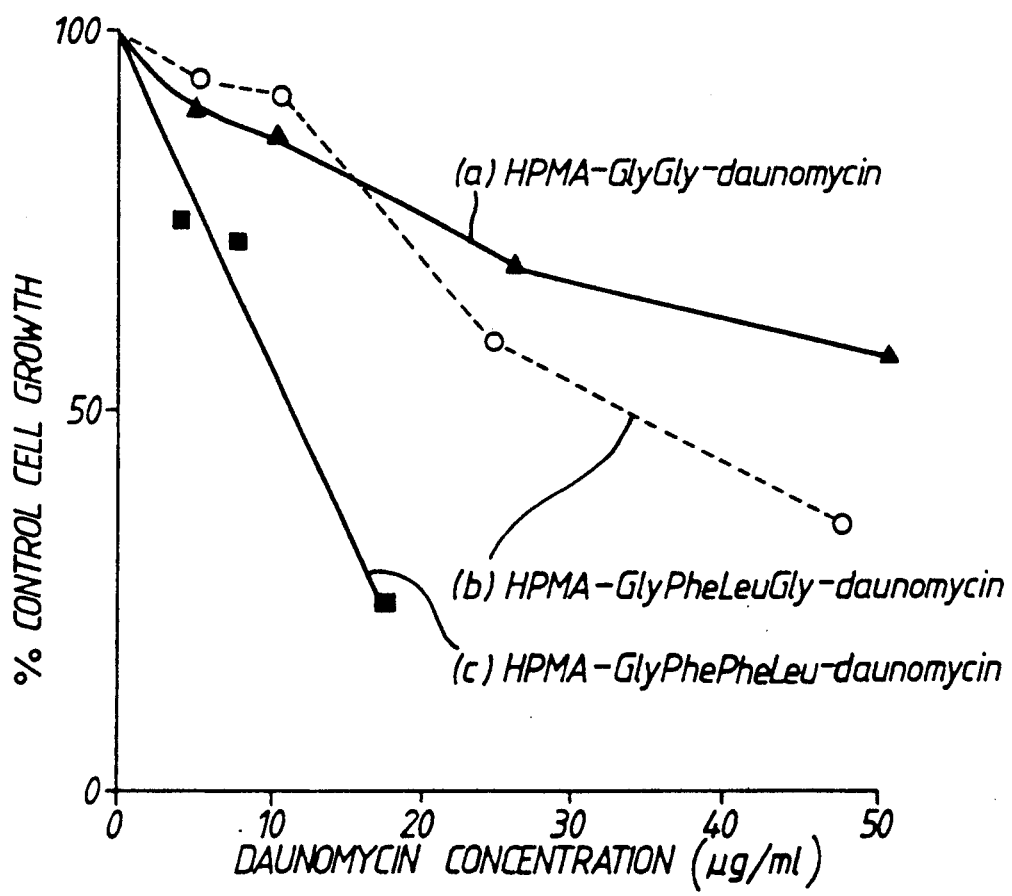
FIG. 1 is a graphical depiction of the percentage of control cell growth versus daunomycin concentration, showing the effect of HPMA-daunomycin copolymers on activity of L1210 mouse leukaemia in vitro, as described in Example 22.

The present invention is based on the discovery of (i) peptide groups which can act as spacers which undergo lysosomal hydrolysis at a satisfactory rate to give controlled intracellular drug release and (ii) combinations of linkage and determinant which can be used to bind the determinant to the polymeric chain without interfering with its targeting mechanism, the peptide sequences of (i) and the linkages of (ii) being, at the same time, resistant to extracellular hydrolysis. Other peptide linkages have been developed for the facile lysosomal cleavage of peptide cross-linking spacer. The hydrolysis of these linkages is particularly susceptible to steric hindrance by the polymer chains, more so than the hydrolysis of terminal moieties from peptide side-chains.

According to the present invention, there is provided a polymeric drug comprising an inert synthetic polymeric carrier combined through peptide spacers with a bioactive molecule, and with a targeting moiety, and an optional cross-linkage, which comprises (a) 5.0 to 99.7 mol % of units derived from N-(2-hydroxypropyl)methacrylamide, (b) 0.2 to 20.0 mol % of units derived from an N-methacryloylated peptide, the peptide groups being bound to a bioactive molecule and being Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, or Gly-Gly-Phe-Leu-Gly-Phe, and being subject to intracellular lysosomal hydrolysis, (c) 0.1 to 94.8 mol % of units derived from N-methacrylamide, N-methacrylic acid or an N-methacryloylated aminoacid or peptide, to which are bound a determinant capable of interacting with specific receptors on cell surfaces, the aminoacid or peptide being Leu, Phe, Gly-Gly, Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, or Gly-Gly-Phe-Leu-Gly-Phe, (d) optionally, 0 to 5 mol % of units derived from an N-methacryloylated peptide, the peptide groups being bound to a linking group which is similarly attached to a similar peptide group attached to another polymer chain, the peptide being Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, or Gly-Gly-Phe-Leu-Gly-Phe, and (e) optionally, as a bioassay label, 0 to 2 mol % of units derived from N-methacryloylated tyrosinamide.

Not all combinations of peptide groups listed for feature (b) and bioactive or drug molecules are subject to intracellular lysosomal hydrolysis; thus, as shown below, the combination of Gly-Gly with daunomycin is not subject to such hydrolysis and Gly-Gly should not, therefore, be used as a peptide spacer with daunomycin. However, Gly-Gly is an acceptable spacer for other drugs, such as deacetyl colchicine and colcemid.

As indicated above, in connection with feature (c), the determinant may be linked directly to the polymer chain either by an amide or an ester bond, that is without a spacer, or may be linked through an aminoacid or peptide spacer. The considerations affecting the choice of linkage to be used for any particular determinant are complicated and depend, inter alia, on the nature and number of the drug-bearing units, on whether the polymer is single chain or cross-linked, and, of course, on the nature of the determinant. The overriding requirement is that the determinant should be accessible by the specific receptors on the target cells; this is to a large extent a function of the geometry of the polymeric drug molecule.

The bioactive molecule present in the polymeric drug is preferably an anti-cancer agent, an antimicrobial agent, an antiparasitic agent, an anti-inflammatory agent, a cardio-vascular drug, or a drug acting on the nervous system. Particularly preferred bioactive molecules are, for example, daunomycin, puromycin, adriamycin, melphalan isopropylester (sarcolysine), bleomycin, desferioxamine, bestatin, and tritylcysteine.

The determinant is preferably a monosaccharide, disaccharide, oligosaccharide or O-methacryloylated saccharide unit which is preferably bound by an amide bond, an antibody, such as IgG (rat immunoglobulin) or anti-⊖ antibody, or a protein, such as transferrin or melanocyte-stimulating hormone (MSH). Particularly preferred determinants are galactose, galactosamine, glucosamine, mannosamine, and fucosylamine.

The linking group is preferably of the type -(aminoacid)NH(CH$_2$)$_x$NH(aminoacid)-, where x is an integer from 1 to 12, and is attached to the adjacent peptide spacers by amide bonds. Particularly preferred linking groups are those in which x is 6 and the aminoacid is Phe, Tyr, Ala, Gly or Leu and that in which x is 2 and the aminoacid is Ala.

A particularly preferred embodiment of the invention comprises single or cross-linked chains of the specified polymer with daunomycin as the bioactive molecule, galactose, galactosamine or fucosylamine as the determinant, Gly-Phe-Leu-Gly as the peptide spacer to both the daunomycin and the determinant, and optionally, Gly-Phe-Leu-Gly as the peptide cross-linking spacer and -(Phe)NH(CH$_2$)$_6$NH(Phe)-as the linking group.

The invention also includes the synthesis of polymeric drugs according to the invention.

Since the same peptide-spacer may be used both for the bioactive molecule and the determinant and the preparation of such compounds is simpler than those in which such spacers are different, a synthetic procedure for the former compounds will first be described. The synthesis consists essentially of two steps.

The initial step involves the copolymerisation of HPMA and the p-nitrophenyl ester of the N-methacryloylated peptide (N-methacryloylated tyrosinamide may also be incorporated at this point to provide a bioassay label) to give a "polymeric precursor" in which the terminal p-nitrophenoxy groups on the peptide side-chains are convenient leaving groups for subsequent addition reactions. The second step involves the sequential addition of the reactive drug, the reactive determinant, and optionally, a diamino cross-linking agent. If the single chain form of the polymeric drug carrier is required, the drug and determinant are consecutively added to the polymeric precursor in either order. If the cross-linking product is required, a suitable cross-linking agent, the drug, and the determinant are sequentially added to the polymeric precursor, again in any desired order.

The above process may be represented as follows:

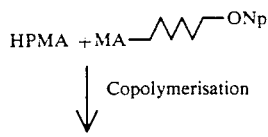

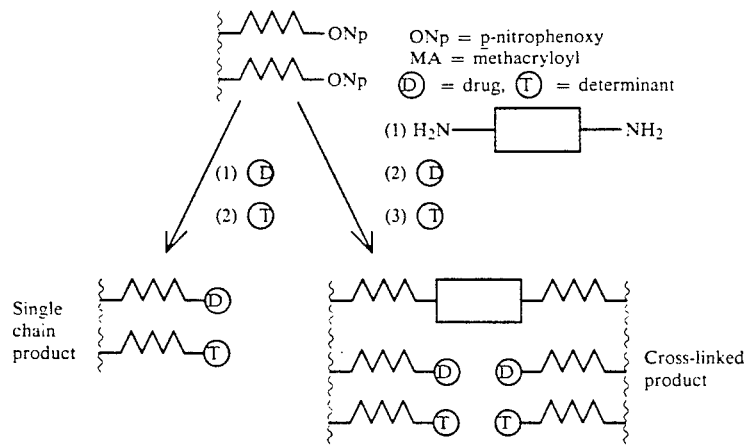

In those cases in which the drug and the determinant linkages are not the same, two synthetic routes are available.

For those cases in which the drug and determinant linkages have common aminoacid residues adjacent to the carrier, the polymeric precursor containing these aminoacids is sequentially treated with an aminoacid or peptidyl derivative of the drug, an aminoacid or peptidyl derivative of the determinant, and, optionally, when a cross-linked product is required, a diamino cross-linking agent.

This procedure may be represented as follows:

Alternatively, the determinant may be bound to an N-methacryloylated peptide having the required aminoacid sequence for the determinant spacer and the N-methacryloylated peptidyl determinant then incorporated in the copolymerisation step. The polymeric precursor is consecutively treated with the reactive drug and, optionally, when a cross-linked product is required, a diamino cross-linking agent.

This procedure may be represented as follows:

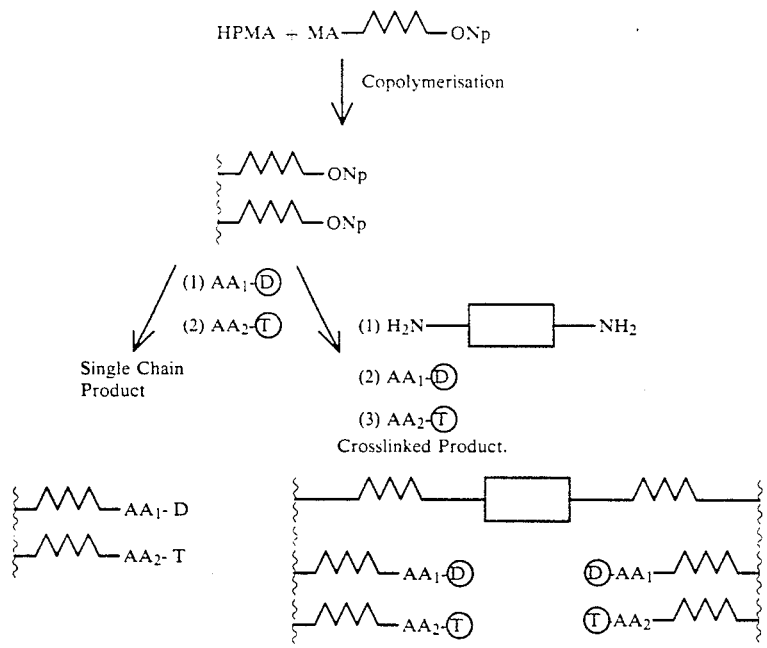

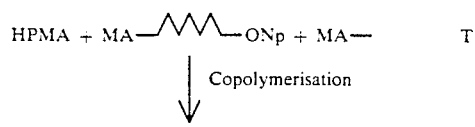

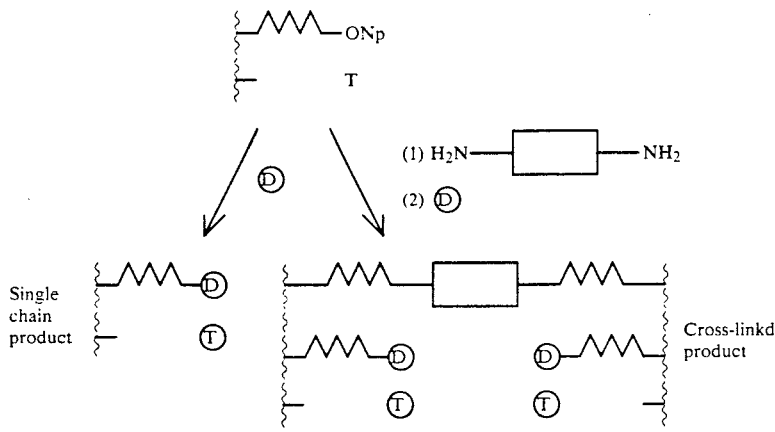

It is also possible to prepare polymeric precursors similar to those described above, but containing peptide side-chains which terminate not in p-nitrophenyl ester groups, but in carboxyl groups. In the presence of a suitable catalyst, reactive drugs and determinants may be attached to these polymeric precursors through the terminal carboxyl groups; hydroxy rather than p-nitrophenoxy is the nominal leaving group during addition.

Drugs and determinants with reactive amino groups give products which are identical to those obtained from polymeric precursors with terminal p-nitrophenyl ester groups, that is, the reactive molecule is attached to the side-chain through an amide bond. However, polymeric precursors with terminal carboxyl groups, in contrast to those with terminal p-nitrophenyl ester groups, also react with drugs and determinants with reactive hydroxy groups to give products in which the reactive molecule is attached to the side-chain through an ester bond.

Polymeric precursors with side-chains terminating in carboxyl groups may be prepared (a) by base hydrolysis of the corresponding polymeric precursor with side-chains terminating in p-nitrophenyl ester groups, the preparation of which has been described above, or (b) by copolymerising HPMA in accordance with any of the synthetic procedures described above for the preparation of the polymeric precursor with terminal p-nitrophenyl ester groups, but using in the copolymerisation step non-esterified N-methacryloylated peptide rather than the p-nitrophenyl ester thereof. The resultant copolymer may then be consecutively treated with the reactive drug and the reactive determinant.

The methods by which polymeric precursors with side-chains terminating in carboxyl groups may be prepared may be represented as follows:

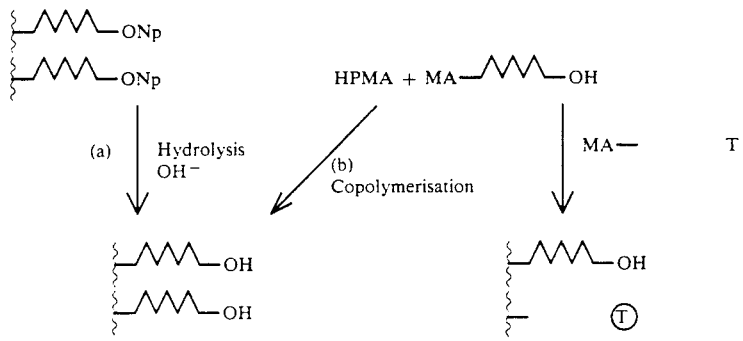

Suitable catalysts for the addition of the reactive drug and/or determinant to polymeric precursors containing carboxyl groups include carbodiimides, such as dicyclohexylcarbodiimide in organic solvents and N-cyclohexyl-N'-(2-morpholino ethyl) carbodiimide metho-p-toluenesulphonate in aqueous solutions, and Woodward's reagent (N-ethyl-5-phenylisoxazolium-3'-sulphonate).

The order in which any or all of the reactive drug, reactive determinant, and cross-linking agent are added to the polymeric precursors in any of the above synthetic procedures is not critical. The amounts of the reactants used should, of course, be those which give the desired molar contents of each component in the polymer within the ranges specified above. The overall molecular weight is determined by the polymerisation conditions, particularly the concentration of initiator, the presence of transfer agents, and the concentration of comonomer p-nitrophenoxy groups.

The single chain products according to the invention preferably have a molecular weight in the range 5,000 to 60,000, more preferably 30,000 to 60,000, and the cross-linked products preferably in the range 10,000 to 500,000, more preferably 30,000 to 400,000.

The starting materials required to carry out the syntheses described above are either currently available or can be prepared by general methods known to those skilled in the art.

Thus, the peptide derivatives required for copolymerisation with HPMA may be prepared and the copolymerisation may be carried out, as follows:

(i) A commercially available dipeptide (which contains the first two aminoacid residues of the required peptide spacer) is N-methacryloylated as described, for example, in *Makromol. Chem.*, 177, 2833 (1976). (N-methacryloylated tyrosinamide for bioassay purposes may be prepared in the same way).

(ii) The N-methacryloylated dipeptide is then esterified with p-nitrophenol as described, for example, in *Makromol. Chem.*, 178, 2169 (1977). (The N-methacryloylated p-nitrophenyl esters of Leu and Phe which provide the aminoacid spacers which may be used for the determinant may be prepared in the same way).

(iii) The peptide chain of the N-methacryloylated dipeptidyl p-nitrophenyl ester is then extended (unless the dipeptide is Gly-Gly when the dipeptide itself forms one of the spacers which may be used for the determinant) to give the desired peptide sequence by the addition of a peptide containing the necessary aminoacid residues, as described, for example, in *Makromol. Chem.*, 182, 1917 (1981).

(iv) The N-methacryloylated peptide obtained from (iii) may be copolymerised with HPMA to give a polymeric precursor with side-chains having terminal carboxyl groups or it may be reesterified with p-nitrophenol. In the latter case, the N-methacryloylated peptidyl p-nitrophenyl ester may be copolymerised with HPMA as described, for example, in *J. Polymer Sci.*, Polymer Symp. 66, 15 (1979), or, if the drug and determinant are to have different spacers, it may be treated with the reactive determinant to give the N-methacryloylated oligopeptidic determinant and then copolymerised with an N-methacryloylated ester and HPMA as described, for example, in *Biochim. Biophys. Acta*, 755, 518 (1983).

The preparation of HPMA is described in *Angew. Makromol. Chem.*, 70, 109 (1978); the reactive drugs and determinants are all commercially available. Aminoacid and peptidyl derivatives of drugs and determinants may be prepared by methods described in *Makromol. Chem.*, 184, 1997 (1983) and the cross-linking agents may be prepared as described, for example, in *Makromol. Chem.*, 182, 1899 (1981).

The present invention also comprises pharmaceutical compositions which comprise at least one polymeric drug according to the invention and an inert, physiologically acceptable carrier. The polymeric drugs can be administered orally or by injection, for example by intraperitoneal, intravenous or intramuscular injection.

Any of the excipients and drug formulation additives which are conventionally used in such pharmaceutical compositions can, in principle, be used with the polymeric drugs according to the invention. In the case of injectible formulations, it is preferred to use sterile aqueous media as the carrier.

In order that the invention may be more fully understood, the following examples are given by way of illustration.

Examples 22 to 35 are concerned with the biological testing of polymeric drugs according to the invention and analogues thereof, and the remaining examples are concerned with the synthesis of such polymeric drugs.

As indicated, a number of Examples 22 to 35 are concerned with the biological testing of analogues of polymeric drugs according to the invention, these analogues being compounds that include feature (a) and, in some cases, one or both of the optional features (d) and (e), of compounds according to the invention, but only contain one of features (b) and (c) and not both. Analogues were used in these examples rather than compounds according to the invention so that the effect of variation in features (b) and (c) individually could be more clearly demonstrated.

EXAMPLE 1

Preparation of a single chain polymer containing daunomycin bound to tetrapeptide spacer, galactosamine bound to dipeptide spacer and tyrosinamide bound directly to the main chain.

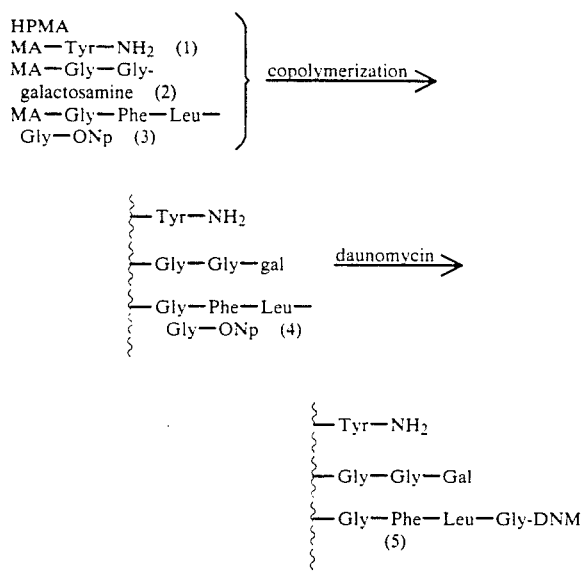

PREPARATION OF MA-Tyr-NH$_2$ (1)

MA-Tyr-NH$_2$ was prepared by reaction of 3.4 g (0.017 mol) p-nitrophenylmethacrylate with 3.0 g (0.017 mol) Tyr-NH$_2$ in dimethylformamide and stirring the reaction mixture for 16 h at 25° C. After evaporating the solvent, the viscous oil was mixed with dry ether and a small amount of hydroquinone. Yield: 3 g of solid product. (M.p. 194°-6° C.; crystallized from ethanol). Molar extinction coefficient, $\epsilon_{280}$ nm $= 1.7 \times 10^3$ (ethanol).

PREPARATION OF MA-Gly-Gly-GALACTOSAMINE (2)

To a mixture of 3.5 g ($1.08 \times 10^{-2}$ mol) of MA-Gly-Gly-ON$_p$ (methacryloyl-glycylglycine p-nitrophenylester) and 2.8 g ($1.3 \times 10^{-2}$ mol) of galactosamine hydrochloride in 18 ml of dimethylformamide was slowly added 18.2 ml ($1.3 \times 10^{-2}$ mol) of triethylamine and the reaction mixture was stirred for 16 h at 25° C. The triethylamine hydrochloride was then filtered off and the remainder of the reaction mixture was evaporated to a viscous oil. After adding ethanol and cooling, the crude product was obtained. Recrystalization gave 1.5 g of product; m.p. 112° C. (ethanol).

PREPARATION OF MA-Gly-Phe-Leu-Gly-ONp (3)

A mixture of 4.1 g ($1.0 \times 10^{-2}$ mol) of MA-Gly-Phe-ONp (prepared according to *J. Polym Sci.*, 66, 15 (1979) in 50 ml dioxan, 2.1 g ($1.1 \times 10^{-2}$ mol) of H-Leu-Gly-OH in 50 ml H$_2$O and 1.8 g ($2.2 \times 10^{-2}$ mol) of NaHCO$_3$ was stirred for 48 h at room temperature. The solvent was evaporated off under reduced pressure to reduce the volume of the mixture to a quarter of its initial volume and after adding a small amount of inhibitor (hydroquinone), the reaction mixture was acidified with dilute hydrochloric acid to a pH of 2. The crude product was extracted into ethyl acetate and precipitated with diethyl ether. Yield: 74% of MA-Gly-Phe-Leu-Gly-OH; m.p. 145°–150° C. TLC analysis showed that the product did not contain impurities. [Note: It was preferred to use the crude product for the next reaction step as the pure material readily polymerises during purification].

4.6 g ($1.0 \times 10^{-2}$ mol) of MA-Gly-Phe-Leu-Gly-OH was esterified with p-nitrophenol ($1.1 \times 10^{-2}$ mol) in 55 ml of THF by means of dicyclohexylcarbodiimide (DCC) ($1.1 \times 10^{-2}$ mol). After 3 hours at 15° C. and 12 hours at 25° C., the dicyclohexylurea was filtered off and the remaining solution was evaporated under reduced pressure. The residue was solidified by adding dry ethyl ether and after recrystalisation from acetone:ether (3:1) gave MA-Gly-Phe-Leu-Gly-ONp in 76% yield which was analytically pure; m.p. 124°–8° C. Aminoacid analysis gave Gly:Leu:Phe of 2.0:1.0:0.99.

PREPARATION OF REACTIVE POLYMERIC PRECURSOR (4)

Copolymerization of HPMA+MA-Tyr-NH$_2$ (1)+MA-Gly-Gly-galactosamine (2)+MA-Gly-Phe-Leu-Gly-ONp (3):

To a solution of 2.5 g ($1.75 \times 10^{-2}$ mol) of HPMA (92 mol %), 0.047 g ($1.90 \times 10^{-4}$ mol) of MA-Tyr-NH$_2$ (1 mol %), and 0.555 g ($9.54 \times 10^{-4}$ mol) of MA-Gly-Phe-Leu-Gly-ONp (5 mol %) in 25 ml acetone was added a solution of 0.138 g ($3.82 \times 10^{-4}$ mol) of MA-Gly-Gly-gal (2 mol %) in 1 ml of DMSO. A solution of 0.153 g of azobisisobutyronitrile in 3 ml acetone was then added. The mixture was poured into ampoules, the ampoules were bubbled through with nitrogen and sealed, and the mixture was polymerized at 50° C. for 24 hours. The precipitated polymer was separated and purified by dissolving in methanol and reprecipitating into acetone. The yield was 1.9 g (60%). The product contained 4.7 mol % of -Gly-Phe-Leu-Gly-ONp side chains (determined from $\epsilon_{274}$ nm$=9.5 \times 10^3$ in DMSO), 1.8 mol % of -Gly-Gly-galactosamine side chains (determined using GPC after acid hydrolysis), and 1.0 mol % of -Tyr-NH$_2$ side chains. $\overline{M}_w$ of aminolysed polymer$=22\,000$; $\overline{M}_w/\overline{M}_n=1.4$.

PREPARATION OF POLYMER CONTAINING DAUNOMYCIN (5)

BINDING OF DAUNOMYCIN TO POLYMER PRECURSOR (4)

To a solution of 1.0 g of copolymer (4) containing $2.8 \times 10^{-4}$ mol of reactive p-nitrophenoxy groups in 4 ml of dimethylsulphoxide (DMSO), a solution of 0.16 g ($2.8 \times 10^{-4}$ mol) of daunomycin hydrochloride in 1 ml DMSO was added, followed by 0.028 g ($2.8 \times 10^{-4}$ mol) of triethylamine. The mixture was stirred at room temperature in the dark for 16 hours and then 20 $\mu$l of aminopropanol was added to remove remaining -ONp groups (if any). The polymer was precipitated by pouring the mixture into 400 ml of acetone/diethylether (9:1) mixture; the precipitate was filtered off, thoroughly washed with acetone and ether, and dried. The polymer was purified by double gel filtration using Sephadex LH-20 (2$\times$100 cm) and methanol as the eluent. The methanol was evaporated under reduced pressure and pure polymer was isolated from water solution by freeze drying. Yield: 0.75 g. Polymer contained 3.5 mol % of side chains terminating in daunomycin (10.2 wt. % of daunomycin), 1.8 mol % of side-chains terminating in galactosamine (1.8 wt. % of galactosamine) and 1 mol % of Tyr-NH$_2$ side chains. The polymer contained less than 0.1% of unbound daunomycin (related to the amount of bound daunomycin).

Determination of unbound daunomycin: free DNM was determined by ethyl acetate extraction: 1.5 mg of the polymer was dissolved of 1 ml of H$_2$O and shaken with a mixture of 1 ml of buffer (0.2M Na$_2$CO$_3$/NaHCO$_3$ pH 9.8) and 2 ml of ethyl acetate. The organic layer was separated, dried with a small amount of dry MgSO$_4$ and the concentration of DNM determined spectrophotometrically at 485 nm ($\epsilon=1.0 \times 10^4$ (ethyl acetate).

EXAMPLE 2

Preparation of single chain polymer containing daunomycin and galactosamine bound to a tetrapeptide spacer and tyrosinamide bound directly to the polymer backbone.

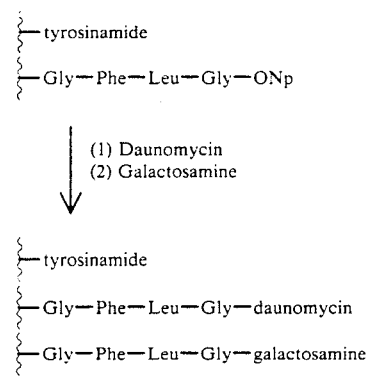

A copolymer of HPMA, MA-tyrosinamide, and MA-Gly-Phe-Leu-Gly-ONp (0.1 g, $2.85 \times 10^{-5}$ mol of -ONp groups) was dissolved in dimethyl sulphoxide (DMSO) (0.4 ml) and a solution of daunomycin hydrochloride (8.5 mg, $1.5 \times 10^{-5}$ mol) in DMSO (0.1 ml) added, followed by triethylamine (1.5 mg, $1.5 \times 10^{-5}$ mol). The mixture was stirred at room temperature for 90 minutes and then a solution of galactosamine hydrochloride (6.5 mg, $3.0 \times 10^{-5}$ mol) in DMSO (0.1 ml) was added, followed by triethylamine (3.0 mg, $3.0 \times 10^{-5}$ mol). The mixture was stirred for 16 hours at room temperature and then poured into an acetone/diethyl ether mixture (9:1). The precipitated polymer was filtered off, thoroughly washed with acetone and diethyl ether, and dried under vacuum. The polymer was purified by dialysis in Visking tubing using dilute acid, then water. The pure polymer was isolated by freeze drying and contained 2.17 mol % of side-chains terminating in daunomycin, i.e. 7.5% by weight of active product, and 1.8 mol % of side-chains terminating in galactosamine, i.e. 2.0% by weight of galactosamine.

EXAMPLE 3

Preparation of single chain polymer containing daunomycin bound to a dipeptide spacer and tyrosinamide bound directly to the polymer backbone.

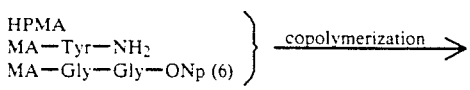

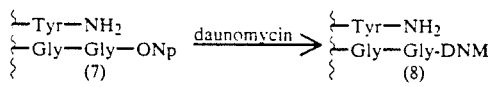

Methacryloylglycylglycine p-nitrophenylester (6) was prepared according to *Makromol. Chem.* 177, 2833 (1976). The preparation of the polymer precursor by copolymerization was carried out as shown in Example 1. $\overline{M}_w/\overline{M}_n = 1.4$ (aminolyzed precursor).

PREPARATION OF POLYMER CONTAINING DAUNOMYCIN (8)

To a solution of 0.50 g of polymer precursor (7) 5.5 mol % of Gly-Gly-ONp side-chains (1.8 $10^{-4}$ mol ONp groups) in 2 ml DMSO 0,038 g ($1.35 \times 10^{-4}$ mol) daunomycin hydrochloride in 0.3 ml DMSO was added, and followed by 0,014 g ($1.35 \times 10^{-4}$ mol) triethylamine. Further procedure was the same as in Example 1. Yield: 0.38 g of polymer containing 3.1 mol % of -Gly-Gly-daunomycin side-chains (10.2 wt. % of daunomycin); $\epsilon_{485}$ nm = 9800 ($H_2O$).

EXAMPLE 4

Preparation of single chain polymer containing daunomycin and anti θ antibodies bound to tetrapeptide side-chain and tyrosinamide bound directly to polymer backbone.

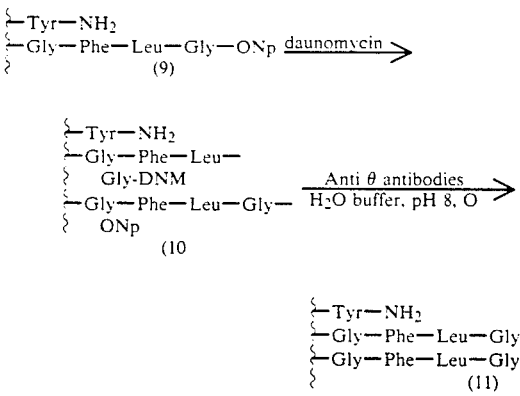

MA-Gly-Phe-Leu-Gly-ONp (3) was prepared as described in Example 1 and polymeric precursor (9) was prepared by copolymerization of HPMA and (3) by the method described in Example 1. Polymer precursor (9) contained 8.0 mol % of -Gly-Phe-Leu-Gly-ONp side-chains and 1 mol % of Try-NH$_2$. $\overline{M}_w$ of aminolyzed precursor (9) = 17 000; $\overline{M}_w/\overline{M}_n = 1.3$.

PREPARATION OF POLYMER WITH DAUNOMYCIN AND FREE REACTIVE GROUPS

To a solution of 0.31 g of polymer precursor (9) (containing $1.35 \times 10^{-4}$ mol of ONp groups) in 1.2 ml DMSO was added 0.028 g ($5.1 \times 10^{-5}$ mol) of daunomycin hydrochloride in 0.1 ml DMSO and 0.0052 g ($5 \times 10^{-5}$ mol) of triethylamine. The reaction mixture was stirred at room temperature for 60 minutes and then poured into 400 ml of acetone: ether (3:1) mixture to precipitate the polymer. The polymer contained 2.5 mol % of side-chains terminating in daunomycin and 4.3 mol % of side-chains terminating in unreacted ONp groups.

BINDING OF ANTI-θ ANTIBODIES TO POLYMER CONTAINING DAUNOMYCIN 77 mg of the copolymer described in the preceding paragraph was dissolved at 5° C. in 0.5 ml of dilute hydrochloric acid (pH 3.0). 0.6 ml of Sorensen buffer (pH 8.0) containing 0.15M NaCl was then added, followed by the dropwise addition of 0.67 ml of anti θ antibody solution in the same buffer (containing 39.5 mg of protein). The reaction was allowed to proceed for 30 minutes at 5° C. During the following 30 minutes the temperature was gradually increased to 20° C. (At the beginning of the reaction, the molar ratio of reactive groups ONp:NH$_2$ = 1:1 and the concentration of macromolecules was 6.6% wt.). After one hour of reaction a solution of 20 μl of 1-aminopropan-2-ol in 0.2 ml of Sorensen's buffer (pH 8.0) containing 0.15M NaCl was added. After 10 minutes the reaction mixture was transferred into a Visking dialysis tubing and dialyzed against phosphate buffered saline (pH 7.2).

EXAMPLE 5

Preparation of single chain polymer containing puromycin and galactosamine bound to tetrapeptide spacer.

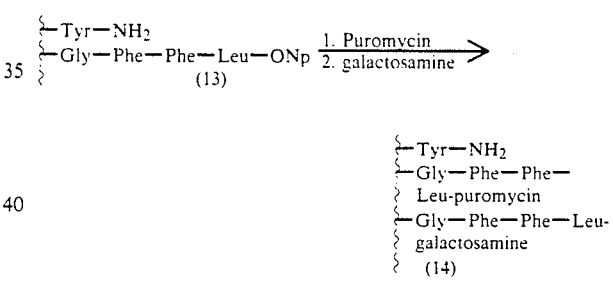

PREPARATION OF MA-Gly-Phe-Phe-Leu-ONp (12)

A mixture of 4.1 g ($1.0 \times 10^{-2}$ mol) of MA-Gly-Phe-ONp (cf. Example 1) in 50 ml of dioxan and 3.06 g ($1.1 \times 10^{-2}$ mol, Sigma) of H-Phe-Leu-OH in 50 ml of dioxan and 1.85 g of NaHCO$_3$ ($2.2 \times 10^{-2}$ mol) in 50 ml of H$_2$O was stirred at room temperature for 45 hours. The further procedure was similar to the preparation of (3) in Example 1. The rough product (yield: 51%) MA-Gly-Phe-Phe-Leu-OH was esterified with p-nitrophenol by the method described in Example 1. After recrystalization from acetone: ether (3:9) mixture, the pure product was obtained in 50% yield. Aminoacid analysis gave Gly: Phe: Leu of 1.0:1.98:1.0.

PREPARATION OF POLYMER PRECURSOR (13)

Copolymerization of HPMA (95 mol %) with MA-Tyr-NH$_2$ (1 mol %) and MA-Gly-Phe-Phe-Leu-ONp (12) (5.0 mol %) according to the procedure described in Example 1 gave a polymer precursor containing 3.0 mol % of -Gly-Phe-Phe-Leu-ONp side-chains and 1.0 mol. of Tyr-NH$_2$ side-chains. $\overline{M}_w$ 23 000; $\overline{M}_w/\overline{M}_n$ 1.3.

BINDING OF PUROMYCIN AND GALACTOSAMINE

To a solution of 0.36 g of polymer precursor (13) (containing $6.5 \times 10^{-5}$ ONp groups) in 1.4 ml DMSO was added a solution of 0.026 g ($4.4 \times 10^{-5}$ mol) of puromycin dihydrochloride in 0.1 ml DMSO and 0.0088 g ($8.8 \times 10^{-5}$ mol) of triethylamine. After stirring for 30 minutes at room temperature, 0.094 g ($4.4 \times 10^{-5}$ mol) of galactosamine and 0.044 g ($4.4 \times 10^{-5}$ mol) of triethylamine were added to the mixture. The reaction mixture was stirred for 16 hours and then 10 µl of aminopropanol was added. The polymer was immediately precipitated in 400 ml of acetone, washed and dried. The polymer was reprecipitated from methanol solution with acetone and purified by the dialysis of water solution in Visking dialysis tubing. After isolation of the product by lyophylization, 0.265 g of the polymer was obtained containing 1.3 mol % of side-chains terminating in puromycin (3.7 wt. % of puromycin: determined from molar extinction coeficient $\epsilon_{272\ nm} = 2.0 \times 10^4$, ethanol) and 1.0 mol % of side-chains terminating in galactosamine (1.0 wt. % of galactosamine). The purity of the product, i.e. the presence of low-molecular puromycin; was checked by extraction of the polymer into ethyl acetate as described in Example 1 and confirmed by GPC on Sephadex G-15.

EXAMPLE 6

Preparation of single chain polymer containing deacetylcolchicine bound to tripeptide spacer and small amount of Tyr-NH$_2$

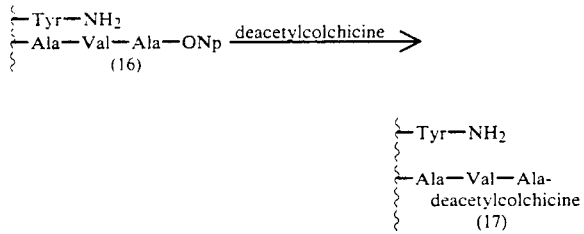

PREPARATION OF MA-Ala-Val-Ala-ONp (15)

15 g (0.17 mol) of alanine was dissolved in 40 ml of methanol and 20 g of thionyl chloride was slowly added to the solution at $-15°$ C. After 1 h at room temperature and 2 h of boiling and removal of methanol, 12 g of HCl. Ala-OMe was isolated using diethyl ether.

To a solution of 10 g (0.086 mol) of valine and 3.4 g (0.086 mol) of NaDH in 250 ml of dioxan: H$_2$O (2:1) mixture was slowly added 20.5 g (0.094 mol) of ditert-butylcarbonate at 0° C. with vigorous stirring. The reaction mixture was then stirred for another hour at room temperature, dioxan was removed under reduced pressure, and BOC-Val-OH was obtained by acidifying the mixture to a pH of 2-3. The raw product consisting of 18 g of viscous oil was obtained after evaporating the solvent from the ethyl acetate extracts.

The condensation of BOC-Val-OH with HCl. Ala-OMe was carried out by a mixed anhydride method. 12 g (0.055 mol) of BOC-Val-OH was dissolved in 40 ml of dry THF and 5.6 g (0.055 mol) of triethylamine and 6.6 g (0.06 mol) of chloroformic acid ethyl ester was added to the solution after cooling to $-15°$ C. After 10 minutes at low temperature 7.7 g (0.055 mol) of HCl.Ala-OMe and 5.6 g (0.055 mol) of triethylamine were slowly added to the mixture at $-15°$ C. The reaction mixture was stirred for a further 16 hours at room temperature. The THF was evaporated and the product extracted with ethyl acetate. Recrystalization from ether gave 8.1 g of analytically pure BOC-Val-Ala-OMe, m.p. 138°-148° C.

Removal of the BOC-group was carried out by dissolving 8.1 g of the BOC-Val-Ala-OMe in 60 ml of methanol and adding 20 ml of 30% HCl methanol. After 2 hours of stirring, the solvent was evaporated and raw HCl.Val-Ala-OMe was isolated.

Using the Schotten-Bauman method of acylation, N-methacryloylalanine was prepared. Coupling of MA-Ala-OH (5.35 g; 0.034 mol) with HCl.Val-Ala-OMe (8.1 g) was performed in dimethylformamide by means of dicyclohexylcarbodiimide (7.0 g) in the presence of triethylamine (3.4 g). Recrystalization from CH$_2$Cl$_2$/pentene gave 9.5 g of MA-Ala-Val-Ala-OMe.

8 g of MA-Ala-Val-Ala-OMe was hydrolysed in methanol with a small excess of 2N NaOH followed by acidification (after removal of the methanol) with citric acid to a pH of 3. 4 g of the raw product was used in the following reaction.

From 3.6 g of MA-Ala-Val-Ala-OH (0.012 mol), 1.5 g (0.012 mol) of p-nitrophenol, and 2.5 g (0.0125 mol) of dicyclohexylcarbodiimide in 50 ml of tetrahydrofuran was prepared 2.0 g (40% yield) of MA-Ala-Val-Ala ONp; m.p. 174°-6° C. Recrystalized from ethylacetate/hexane. Molar extinction coefficient, $\epsilon_{274\ nm} = 9300$ (DMSO).

PREPARATION OF POLYMER PRECURSOR

Copolymerization of HPMA (95 mol %), MA-Tyr-NH$_2$ (1 mol %) and MA-Ala-Val-Ala-ONp (4 mol %) gave a polymer precursor containing 2.9 mol % of side-chains with ONp groups. $\overline{M}_w$ 27,000; $\overline{M}_w/\overline{M}_n$ 1.4 (determined for aminolyzed precursor).

The mixture of deacetylcolchicine and isodeacetylcolchicine was prepared by treating trimethylcolchicinic acid with diazomethane according to a known procedure (Biochemistry 25, 2463 (1966)).

BINDING OF DEACETYLCOLCHICINE

To a solution of 0.41 g of polymer precursor (16) (containing $4.0 \times 10^{-5}$ mol of ONp groups) in 1.6 ml of DMSO was added a solution of 0.021 g ($6.0 \times 10^{-5}$ mol) of deacetylcolchicine in DMSO. The mixture was stirred for 20 hours at room temperature in the dark and the polymer then precipitated in acetone. Purification was carried out by ultrafiltration (UM-02 membrane) in H$_2$O with 20% methanol. The polymer product isolated by lyophilisation contained 2.7 mol % of side-chains terminating in deacetylcolchicine. (Calculated from molar extinction coefficient, $\epsilon_{350\ nm} = 1.6 \times 10^4$ (ethanol)).

EXAMPLE 7

Preparation of crosslinked polymer containing daunomycin and galactosamine prepared by consecutive aminolysis.

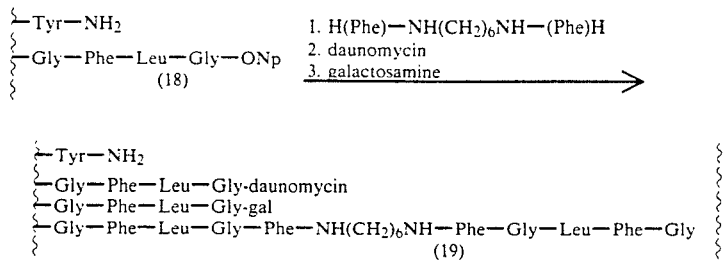

Polymer precursor (18) was prepared by copolymerization of HPMA (90 mol %), MA-Tyr-NH$_2$ (1 mol %), and MA-Gly-Phe-Leu-Gly-ONp (9.0 mol %). Polymer precursor (18) contained 8.0 mol % of side-chains terminating in ONp groups. $\overline{M}_w = 17\,000$; $\overline{M}_w/\overline{M}_n = 1.3$. (determined for aminolyzed precursor).

0.2 g of the polymer precursor (18) (8.0 mol % of side chains containing ONp groups) in 0.8 ml DMSO ($9.8 \times 10^{-5}$ mol ONp) was added to a solution of 0.0045 g ($1.1 \times 10^{-5}$ mol) of N,N'-bis(H-phe)hexamethylenediamine in 0.2 ml of DMSO. The mixture was stirred at room temperature for 5 minutes and then a solution of 0.036 g ($6.3 \times 10^{-5}$ mol) of daunomycin hydrochloride in 0.3 ml of DMSO was added followed by 0.0064 g ($6.3 \times 10^{-5}$ mol) of triethylamine. The mixture was stirred for 60 minutes and then a solution of galactosamine hydrochloride (0.018 g: $8.5 \times 10^{-5}$ mol) and triethylamine (0.0086 g; $8.5 \times 10^{-5}$ mol) was added. The mixture was stirred for a further 16 hours and the polymer then precipitated in acetone. The polymer was purified first by gel filtration using Sephadex LH-20/methanol and then by dialysis in Visking dialysis tubing against water. The pure polymer was isolated by freeze drying. The polymer product contained 2.8 mol % of side-chains terminating in daunomycin (7.8 wt. % of daunomycin) (determined from $\epsilon_{485\,nm}$ $9.8 \times 10^3$ (DMSO)), and 3.9 mol % of side-chains terminating in galactosamine. Yield of polymer: 0.15 g; $\overline{M}_w$ 110,000; $\overline{M}_w/\overline{M}_n$ 4.0 ($\overline{M}_w$ of aminolyzed precursor was 17,000; $\overline{M}_w/\overline{M}_n$ 1.3).

EXAMPLE 8

Preparation of single chain polymer containing bleomycin and Tyr NH$_2$ tyrosinamide.

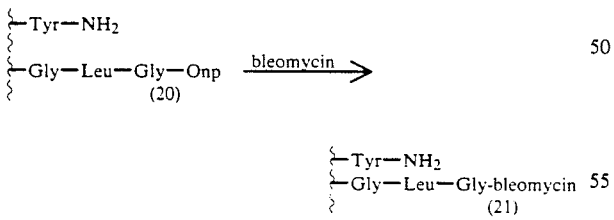

Methacryloylglycylleucylglycine p-nitrophenylester was prepared by the procedure described in Example 6 for compound (15).

The polymer precursor was obtained by the copolymerization of HPMA (94 mol %), MA-Tyr-NH$_2$ (1 mol %) and MA-Gly-Leu-Gly-ONp (5 mol %). The polymer precursor (20) contained 4.3 mol % of side-chains terminating in ONp groups.

To a solution of 0.137 g of precursor (20) ($3.8 \times 10^{-5}$ mol of ONp groups) in 0.55 ml of dimethylsulfoxide was added a solution of 0.047 g ($3.8 \times 10^{-5}$ mol) of bleomycin sulphate and 0.0038 g ($3.8 \times 10^{-5}$ mol) of triethylamine in 0.3 ml of DMSO. The reaction mixture was stirred for 12 hours and the polymer was then isolated by adding 20 μl of aminopropanol and pouring into acetone. After two days of dialysis using Visking tubing the polymer was lyophilized. Yield: 0.102 g. The polymer product contained 3.1 mol % of side-chains terminating in bleomycin (determined by kinetic measurements to determine the concentration of ONp groups).

EXAMPLE 9

Preparation of single chain polymer containing melanocyte-stimulating hormone (MSH) bound to dipeptide spacer.

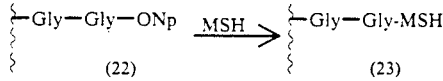

To a solution of 0.20 g of the polymer precursor (22) (5.0 mol % Gly-Gly-ONp) containing $6.6 \times 10^{-5}$ mol of ONp groups in 0.8 ml DMSO was added a solution of 0.005 g ($3.0 \times 10^{-5}$ mol) of melanocyte-stimulating hormone in 0.3 ml of DMSO. After 16 hours of stirring 10 μl of aminopropanol was added and the polymer product precipitated in acetone. After purification using dialysis and lyophilization the product was analyzed to determine the content of bound MSH. The polymer product (23) contained 1.3 wt. % of MSH (determined spectrophotometrically: for 0.347 mg/ml of MSH in H$_2$O, $A_{278\,nm}^{1\,cm} = 1.49$).

EXAMPLE 10

Preparation of single chain polymer containing desferioxamine bound to tetrapeptide spacer.

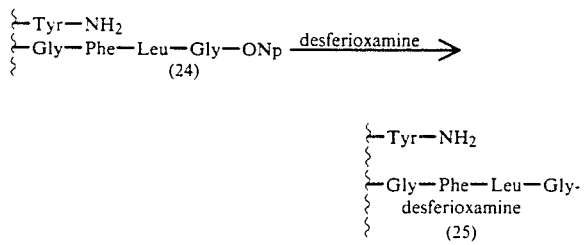

A polymer precursor (24) containing 4.3 mol % of side-chains having ONp groups (0.20 g; $5.3 \times 10^{-5}$ mol of ONp groups) was dissolved in 0.8 ml of DMSO and 0.070 g ($1.06 \times 10^{-4}$ mol) of desferioxamine and 0.011 g ($1.06 \times 10^{-4}$ mol) of triethylamine in 0.2 ml of DMSO were added. After 16 hours of stirring at room temperature, the polymer product was precipitated in 200 ml of acetone. Purification was carried out by dialysis in water containing 20% methanol using Visking dialysis tubing.

The desferioxamine content was calculated by kinetic measurements to determine the amount of ONp groups in the reaction mixture. The polymer product contained 3.9 mol % of side-chains with bound desferioxamine (12.4 wt. % of desferioxamine).

EXAMPLE 11

Preparation of single chain polymer containing bestatin and galactosamine bound to tetrapeptide spacer.

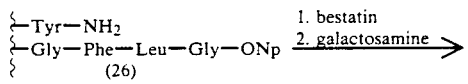

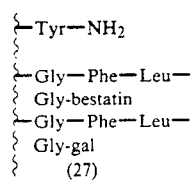

0.150 g of the polymer precursor (18) (containing $6.8 \times 10^{-5}$ mol of ONp groups) was dissolved in 0.6 ml of DMSO and a solution of 0.005 g ($1.45 \times 10^{-5}$ mol) of bestatin and 0.0029 g ($2.9 \times 10^{-5}$ mol) of triethylamine in 0.1 ml of DMSO was added. After 1 hour of stirring at room temperature a solution of 0.030 g (1.3 $10^{-4}$ mol) of galactosamine and 0.014 g ($1.3 \times 10^{-4}$ mol) of triethylamine in 0.2 ml of DMSO was added and the reaction mixture was allowed to stir at room temperature for 16 hours. After that the product was precipitated in 200 ml of acetone and purified by 3 days of dialysis. Lyophilized product (0.111 g) was analyzed for the content of galactosamine (cf. Example 1). The amount of bound bestatin was calculated from kinetic measurement by following the amount of ONp groups in the reaction mixture. The polymer product (27) contained 1.4 mol % of side-chains terminating in bestatin (2.4 wt. % of bestatin) and 5.4 mol % of side-chains terminating of galactosamine (5.5 wt. % of galactosamine).

EXAMPLE 12

Preparation of single chain polymer containing adriamycin and mannosamine bound to tetrapeptide spacer.

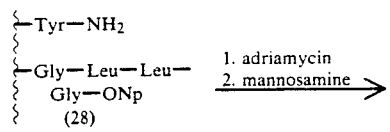

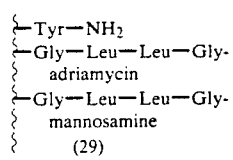

Methacryloylglycylleucylleucylglycine p-nitrophenylester was prepared by a similar procedure to that described in Example 1 for preparing (3).

Polymer precursor (28) was prepared by the copolymerization of HPMA (89.5 mol %), MA-Tyr-NH2 (1 mol %) and MA-Gly-Leu-Leu-Gly-ONp (9.5 mol %).

The polymer contained 8.1 mol % of tetrapeptide sidechains terminating in ONp groups. $\overline{M}_w = 17,000$; $\overline{M}_w/\overline{M}_n = 1.3$ (determined for aminolyzed precursor).

Polymer product (29) was prepared from 0.4 g of the polymer precursor (28) containing $1.8 \times 10^{-4}$ mol of ONp groups dissolved in 1.6 ml of DMSO to which 0.06 g ($1.1 \times 10^{-4}$ mol) of adriamycin hydrochloride and 0.011 g ($1.1 \times 10^{-4}$ mol) of triethylamine in 0.2 ml of DMSO was added. After 1 hour of stirring at 25° C., 0.030 g (1.4 $10^{-4}$ mol) of galactosamine and 0.014 g (1, $4.10^{-4}$ mol) of triethyamine were added to the mixture. The subsequent procedure was the same as that described in Example 1. The polymer product contained 3.2 mol % of side-chains containing adriamycin (9.6 wt. % of adriamycin) and 4.1 mol % of side-chains containing mannosamine. Yield: 0.31 g. The content of sugar residues was determined after acid hydrolysis using GPC according to a known procedure (Anal. Biochem., 73, 532 (1976)).

EXAMPLE 13

Preparation of single chain polymer containing bleomycin bound to tripeptide spacer.

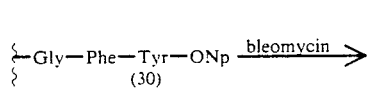

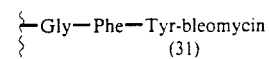

The reactive monomer MA-Gly-Phe-Tyr-ONp and the polymer precursor (30) were prepared according to Makromol. Chem. 182, 799 (1981). The polymer precursor contained 8.5 mol % of side-chains having ONp groups. $\overline{M}_w/\overline{M}_n = 1.3$ (determined for aminolyzed precursor).

The binding of bleomycin to the polymer precursor was carried out by the procedure described in Example 8. The polymer product (31) contained 5.7 mol % of side-chains containing bleomycin.

EXAMPLE 14

Preparation of single chain polymer containing puromycin and fucosylamine bound to tripeptide spacer.

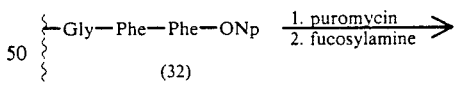

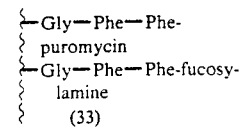

Reactive monomer MA-Gly-Phe-ONp and polymer precursor (32) were prepared according to Makromol. Chem. 182, 799 (1981). The polymer precursor contained 12.9 mol % of side-chains with ONp groups. $\overline{M}_w$ of aminolyzed precursor = 14,000; $\overline{M}_w/\overline{M}_n = 1.28$. To a solution of 0.25 g of the polymer precursor (32) ($1.64 \times 10^{-4}$ mol of ONp groups) in 1 ml of DMSO was added a solution of 0.029 g ($4.9 \times 10^{-5}$ mol) of puromycin dihydrochloride and 0.010 g ($9.8 \times 10^{-5}$ mol) of triethylamine in 0.25 ml of DMSO. The reaction was allowed to proceed for 1 hour and then 0.015 g (9.0 $10^{-5}$ mol) of fucosylamine in 0.1 ml of DMSO was added to the mixture. The subsequent procedure was similar to that described in Example 5. The polymer product (33) contained 4.1 mol % of side-chains terminating in puromycin and 6.7 mol % of side-chains terminating in fucosylamine.

EXAMPLE 15

Preparation of single chain polymer containing transferrin bound to dipeptide spacer.

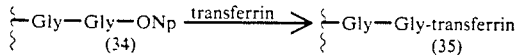

27.4 mg of the polymer precursor (34) containing 11.4 mol % of Gly-Gly-ONp side-chains was dissolved in 0.25 ml of diluted hydrochloric acid (pH 3.0). 1.25 ml of Sørensen buffer (pH 8) containing 0.1M NaCl was then added followed by a solution of 14.2 mg of transferrin in 0.5 ml of the same buffer. After 45 minutes, 10 μl of 1-amino-2-propanol dissolved in 0.2 ml of Sørensen buffer was added to the mixture. After 30 minutes the reaction was stopped and transferred to Visking dialysis tubing and dialyzed against phosphate buffered saline (pH 7.2).

EXAMPLE 16

Preparation of single chain polymer containing IgG bound to dipeptide spacer.

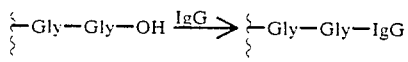

$5.0 \times 10^{-6}$ mol of COOH groups) was dissolved in Sørensen buffer of pH 5 (75 ul) and a solution of N-cyclohexyl-N'-[2-morpholino ethyl]-carbodiimide (0.002 mg) in the same buffer (40 ul) added at 1° C. The mixture was stirred for 15 minutes and then a solution of IgG (60.0 mg) in the same buffer (235 ul) was added slowly. The mixture was stirred for 5 hours and then stood overnight at 4° C. The crude reaction mixture was dialysed against phosphate buffered saline (pH 7.2).

EXAMPLE 17

Preparation of crosslinked polymer containing puromycin and galactosamine bound to tripeptide spacer.

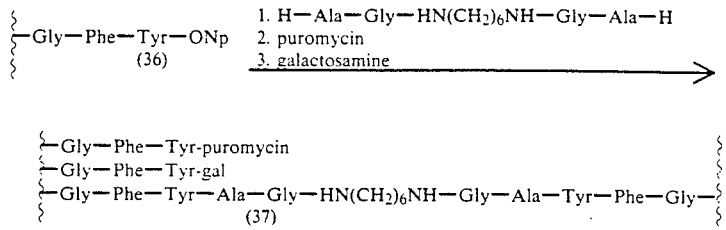

Polymer precursor (36) containing 4.8 mol % of side-chains with ONp groups was prepared according to Makromol. Chem. 182, 1899 (1981).

2.0 g of the polymer precursor (36) containing $5.9 \times 10^{-4}$ mol of ONp groups was dissolved in 8 ml of DMSO and a solution of 0.038 g ($9.8 \times 10^{-5}$ mol) of 1,2-bis(alanylglycylamino)ethane dihydrochloride in 0.2 ml of DMSO was added followed by 0.020 g ($2.0 \times 10^{-4}$ mol) of triethylamine. Crosslinking was carried out for 20 minutes. 0.120 g ($2 \times 10^{-4}$ mol) of puromycin dihydrochloride in 1 ml of DMSO and 0.040 g ($4 \times 10^{-4}$ mol) of triethylamine were then added to the mixture. After stirring the reaction mixture for 1 hour, a solution of 0.129 g ($6.0 \times 10^{-4}$ mol) galactosamine hydrochloride and 0.060 g ($6.0 \times 10^{-4}$ mol) of triethylamine in 1 ml of DMSO was added. The mixture was stirred for 16 hours at room temperature. The product was isolated and purified as described in Example 5. The product contained 1.5 mol % of side-chains terminating in puromycin (4.3 wt. % of puromycin) and 2.8 mol % of side-chains terminating in galactosamine.

EXAMPLE 18

Preparation of crosslinked polymer containing puromycin and fucosylamine bound to tripeptide spacer.

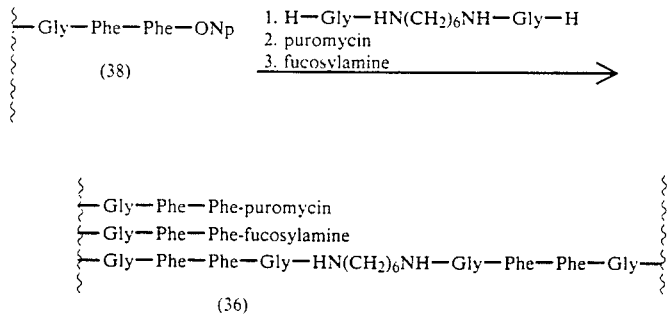

Polymer precursor (38) containing 4.8 mol % of side-chains having ONp groups was prepared according to Makromol. Chem. 182, 1899 (1981).

2.0 g of the polymer precursor (38) containing $5.9 \times 10^{-4}$ mol of ONp groups was dissolved in 8 ml of DMSO and a solution of 0.029 g ($9.8 \times 10^{-5}$ mol) of 1,2-bis(glycylamino)ethane diacetate, prepared according to Makromol. Chem 182, 1899 (1981), in 0.2 ml of DMSO was added, followed by 0.020 g ($2.0 \times 10^{-4}$ mol) of triethylamine. Crosslinking was carried out for 5 minutes. 0.120 g ($2 \times 10^{-4}$ mol) of puromycin dihydrochloride in 1 ml DMSO and 0.040 g ($4 \times 10^{-4}$ mol) diethylamine were then added to the mixture. After stirring the reaction mixture for 1 hour a solution of 0.98 g ($6.0 \times 10^{-4}$ mol) of fucosylamine in 1 ml of DMSO was added. The mixture was stirred for 16 hours at room temperature. The product was isolated and purified as described in Example 5. The product contained 1.4 mol % of side-chains terminating in puromycin (4.2 wt. % of puromycin) and 3.0 mol % of side-chains terminating in fucosylamine.

EXAMPLE 19

Preparation of single chain polymer containing daunomycin bound to tetrapeptide spacer and galactose bound directly to the polymer chain.

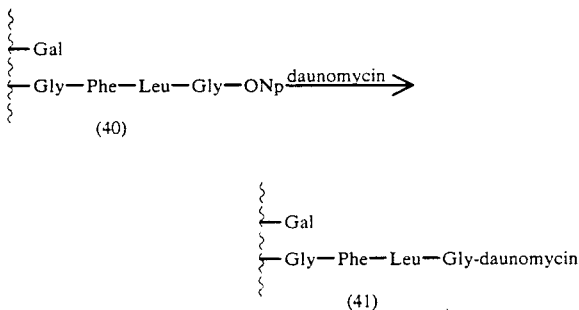

PREPARATION OF POLYMER PRECURSOR (40)

0.71 g ($5 \times 10^{-3}$ mol) HPMA and 1.64 g ($5 \times 10^{-3}$ mol) 1,2,3,4-di-O-isopropylidene-6-O-methacryloyl-α-D-galactopyranose (prepared according to *J. Chem. Soc.* (London) C, 1913 (1966)) were dissolved in 13.0 ml of dimethylsulfoxide. To this solution was added azobisisobutyronitrile (3 mg ($1.8 \times 10^{-4}$ mol) in 1.8 ml of dimethylsulfoxide), followed by MA-Gly-Phe-Leu-Gly-ONp (291 mg ($5 \times 10^{-4}$ mol) in 1.0 ml of DMSO), prepared according to the method described in Example 1. The mixture was bubbled through with nitrogen and then polymerized in a sealed ampoule at 60° C. for 30 hours. The resulting polymer was precipitated in ether and deacetonated by dissolving in 80% aqueous formic acid for 20 hours at room temperature. The yield of the polymer precursor after evaporation of the formic acid was 1.2 g; the content of ONp groups was 9.5 mol % and the content of galactose was 52 mol %.

BINDING OF DAUNOMYCIN TO POLYMER PRECURSOR (40)

374 mg ($1.6 \times 10^{-4}$ mol) of the polymer precursor (40) was dissolved in 1.6 ml of DMSO and daunomycin hydrochloride (50 mg ($8 \times 10^{-5}$ mol) in 0.3 ml DMSO) and triethylamine (0.0111 ml ($8 \times 10^{-5}$ mol)) were added to the solution. The reaction mixture was allowed to stir for 30 minutes at room temperature. 20 µl of aminopropanol was then added and the product immediately precipitated in 200 ml of acetone. The precipitate was dissolved in methanol and the polymer fraction separated using a Sephadex LH-20 column (100×2.5 cm), equilibrated with methanol. The yield was 0.28 g; the content of tetrapeptide side chains terminating in daunomycin was 3.5 mol %.

EXAMPLE 20

Preparation of single chain polymer containing melphalan isopropylester bound to tripeptide spacer and galactose bound directly to the main chain.

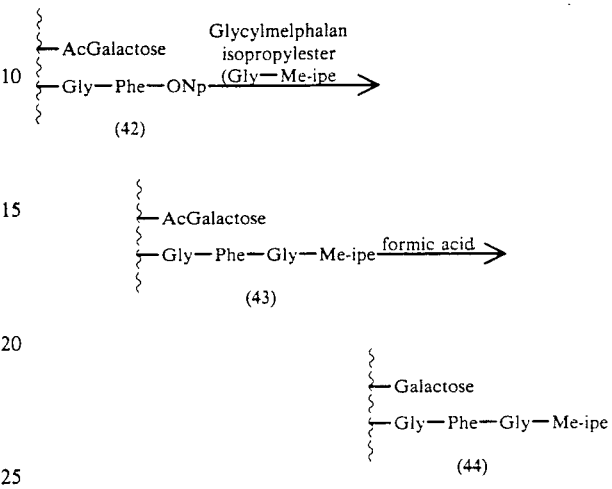

PREPARATION OF MELPHALAN ISOPROPYL ESTER (Me-ipe)

A solution of 5 g of melphalan in HCl-isopropanol (20%) was refluxed for 5 hours. After cooling in a refrigerator, white crystals of analytically pure product were isolated and dried in vacuo, m.p. 200°-201° C. A solution of Me-ipe in 50 ml diethyl ether was bubbled through with $NH_3$ for 3 hours; the solvent was then evaporated and the oily product used for the next synthetic step.

PREPARATION OF GLYCYLMELPHALAN ISOPROPYL ESTER (Gly-Me-ipe)

Gly-Me-ipe was prepared by reacting 3.03 g of BOC-Gly-OH with 6.0 g Me-ipe in 50 ml of tetrahydrofuran using the DCC method. The protecting BOC group was removed in HCl methanol (15%) solution and the free base was prepared by bubbling $NH_3$ through the Gly-Me-ipe hydrochloride suspension in diethyl ether. Ammonium chloride was filtered off and an oily product was isolated after evaporation of the solvent.

PREPARATION OF POLYMER PRECURSOR (42)

Polymer precursor (42) was prepared by radical precipitation copolymerization of DGM (1,2,3,4-di-O-isopropylidene-6-O-methacryloyl-α-D-galactopyranose) and methacryloylglycyl-phenylalanine p-nitrophenylester (Ma-Gly-Phe-ONp) (preparation according to Makromol. Chem. 178, 2169 (1977) as described in Example 1).

Polymerization mixture: HPMA 3.43 g (85 mol %), MA-Gly-Phe-ONp 0.926 g (8 mol %), DGM 0.65 g (7 mol %), Azo-bisisobutyronitrile 0.24 g.

Polymerization carried out for 24 hours at 50° C. in 44 ml of acetone.

BINDING OF Gly-Me-ipe TO THE POLYMER PRECURSOR (42)

3 g of the polymer precursor (42) was dissolved in 20 ml of dimethylsulfoxide and 0.816 g of Gly-Me-ipe was added to the solution. The mixture was stirred at room temperature for 3 days and the polymer then precipitated in acetone and reprecipitated two times from methanol into acetone-diethyl ether (1:1) mixture. Deacetonylation of protected galactose bound to polymer carrier was carried out in 80% formic acid (cf. Example 19) and the polymer drug isolated by lyophilization and precipitation from methanol into acetone-diethyl ether (1:1) mixture. Yield of polymer: 2.9 g. Content of drug bound to polymer carrier (melphalan isopropylester): 106 mg/g of polymer (calculated from elemental analysis less chlorine content). Molecular weight of polymer carrier, $\overline{M}_w = 35,000$. The absence of low molecular compound (free drug) was checked by GPC using Sephadex G-25 as a column packing.

EXAMPLE 21

Preparation of single chain polymer containing melphalan isopropylester bound to tetrapeptide spacer and galactose bound directly to the main chain.

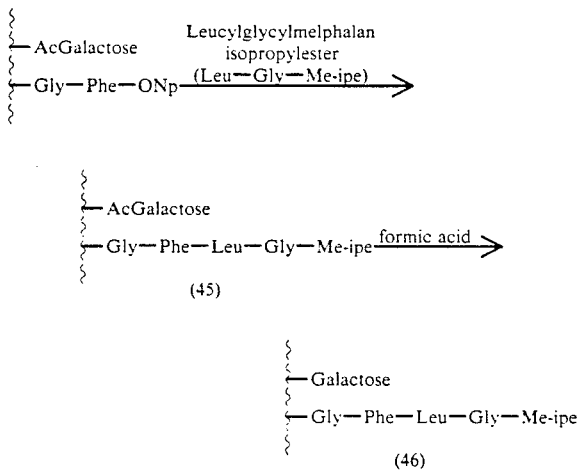

PREPARATION OF LEUCYLGLYCYLMELPHALAN ISOPROPYLESTER 3.1 g of BOC-Leu-Gly-OH was reacted with 3.7 g of Me-ipe in 35 ml of THF using the DCC method. The product BOC-Leu-Gly-Me-ipe was crystal from acetone. The BOC protecting groups were removed in HCl/methanol (15% solution) for 1 hour at 25° C. Yield: 3.2 g of HCl. Leu-Gly-Me-ipe. Free base was prepared by bubbling $NH_3$ through a diethyl ether suspension of the hydrochloride. A pure oily product was isolated after removal of ammonium chloride and evaporation of the solvent. The polymer precursor (42) was prepared by the method described in Example 20.

BINDING OF LEUCYLGLYCYLMEPHALAN ISOPROPYL ESTER TO THE POLYMER PRECURSOR

The reaction was carried out by a similar method to that of Example 18. 0.5 g of Leu-Gly-Me-ipe was added to a solution of 1.5 g of the polymer precursor (42) in 10 ml of DMSO and the mixture was stirred for 3 days. Polymer (45) was precipitated in an acetone-diethyl ether (1:1) mixture and reprecipitated two times from methanol in the same mixture. The deacetonylation of galactose and the isolation and characterisation of polymer (46) were as described in Example 18. $\overline{M}_w$ of polymer carrier: 35,000; content of drug (melphalan isopropylester bound to polymer): 118 mg/g of polymer. The absence of free drug was checked by GPC (Sephadex G-25).

EXAMPLES 22 TO 25

EFFECTS OF DIFFERENT PEPTIDE SPACERS TO SAME DRUG

EXAMPLE 22

(Effect on Activity of L1210 Mouse Leukaemia in vitro)

These experiments were carried out on three HPMA analogues which did not contain determinants. All three analogues contained daunomycin as the bioactive moiety and peptide spacers to the drug in accordance with feature (b). In detail, the analogues were as follows:
  (a) HPMA with -Gly-Gly-daunomycin substituents.
  (b) HPMA with -Gly-Phe-Leu-Gly- daunomycin substituents; and
  (c) HPMA with -Gly-Phe-Phe-Leu- daunomycin substituents.

The mouse leukaemia, L1210, was maintained in suspension culture in RPMI 40 medium containing 10% heat inactivated horse serum. Under these conditions the doubling time was 15-20 h for cell densities up to approximately $1 \times 10^5$ cells per ml. Cell densities were assessed using a Coulter counter.

To evaluate polymeric drug cytotoxicity, cells were seeded into tubes (10 ml) and the starting cell density measured. The various polymeric drugs were added at various concentrations and the cells maintained in a growth cabinet for a further 72 h before measuring cell density.

The number of cells found in tubes containing the polymeric drug was expressed as a percentage of the cells found in tubes incubated for the same period (72 h) without the addition of the drug. The results are shown graphically in FIG. 1 of the accompanying drawings, in which the curves were obtained by plotting percentage cell growth against the daunomycin concentration in μg/ml. The results indicate that all three analogues were cytotoxic to L1210 mouse leukaemia in vitro to some degree, but better inhibitory effects were shown by analogues (b) and (c) than by analogue (a).

EXAMPLE 23

(Effect on Activity of L1210 Mouse Leukaemia in vitro)

These experiments were carried out on three HPMA analogues which did not contain determinants. All three analogues contained sarcolysine (melphalan IPE) as the bioactive moiety and peptide spacers to the drug in accordance with feature (b). In detail, the analogues were as follows:
  (a) HPMA with -GlyLeuGly-sarcolysine substituents;
  (b) HPMA with -GlyPheLeuGly- sarcolysine substituents; and
  (c) HPMA with -GlyPheGly-sarcolysine substituents.

The experimental procedure was the same as that described in Example 22.

Figure 2:
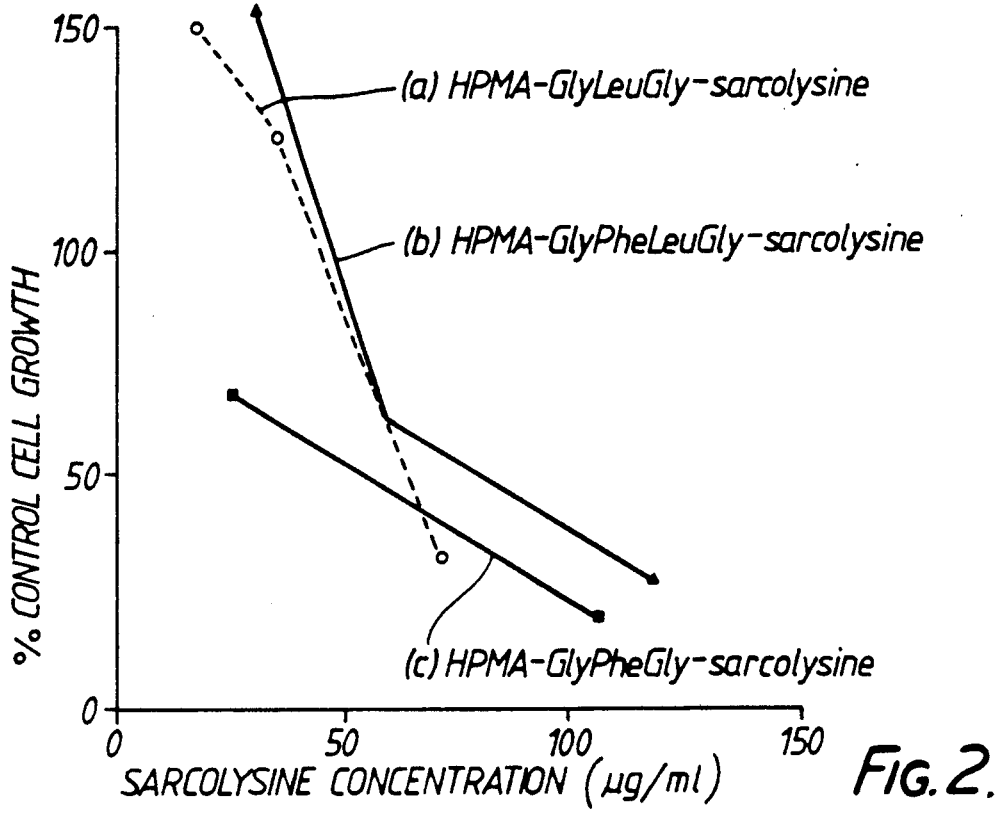
FIG. 2 is a graphical depiction of the percentage of control cell growth versus sarcolysine concentration showing the effect of HPMA-sarcolysine copolymers on activity of L1210 mouse leukaemia in vitro, as described in Example 23.

The results are shown graphically in FIG. 2 of the accompanying drawings, in which the curves were obtained by plotting percentage cell growth against the sarcolysine concentration in μg/ml. The results indicate that all three analogues were cytotoxic to L1210 mouse leukaemia in vitro to some degree, but the inhibitory effect shown by analogue (c) was substantially better than that shown by analogues (a) and (b) which stimulated growth at low concentration.

EXAMPLE 24

(Effect on Activity of L1210 Mouse Leukaemia in vivo)

These experiments were carried out with two HPMA analogues which did not contain determinants; both compounds were of the open chain type. Both analogues contained daunomycin as the bioactive moiety and peptide spacers to the drug in accordance with feature (b). In detail, the analogues were as follows:
(a) HPMA with -GlyPheLeuGly- daunomycin substituents, and
(b) HPMA with -GlyGly- daunomycin substituents.

The mouse leukaemia L1210 was inoculated ($10^5$ viable cells) intraperitoneally into DBA$_2$ mice on day 0. The HPMA copolymers were administered on days 1, 2 and 3. Survival of all animals was monitored. Control (untreated) animals always died between day 15 and day 20.

The results obtained are shown in Table 1.

TABLE 1

| Treatment | Dose (×3) | Mean Survival Time (days) | Long Term Survival (>50 days) |
|---|---|---|---|
| Analogue (a) | 5 mg/kg | 32 | 3/5 |
| Analogue (a) | 2 mg/kg | 31 | 2/5 |
| Analogue (b) | 5 mg/kg | 18 | 1/5 |
| Analogue (b) | 8 mg/kg (×1) +5 mg/kg (×1) | 16 | 1/5 |
| None | — | 17 | 2/10 |

It can be seen from Table 1 that the survival of animals was not prolonged by the administration of analogue (b). In contrast, animals treated with analogue (a) showed markedly prolonged survival, a significant proportion of animals becoming long-term survivors.

EXAMPLE 25

(Effect on Rate of in vitro Release of Drug in Presence of Enzyme)

Two HPMA analogues were prepared which were of the single chain type and did not contain determinants. Both analogues contained daunomycin as the bioactive moiety with different peptide spacers to the drug; both drug spacers were in accordance with the invention. In detail, the analogues were as follows:
(a) HPMA with -GlyPheLeuGly- daunomycin and tyrosinamide substituents, and
(b) HPMA with -GlyPhePheLeu- daunomycin and tyrosinamide substituents.

Each analogue (25 mg in 1.5 ml) was incubated with 1 ml of enzyme solution at 37° C. The enzyme solution was a purified lysosomal enzyme, cathepsin L ($3.8 \times 10^{-7}$ mol/l), in phosphate buffer (pH 6.0) containing 5 mM glutathione and 1 mM EDTA.

At various time intervals release of drug was measured by extracting free drug and measuring absorbance at the appropriate wavelength spectrophotometrically. Samples of the incubation mixture (0.15 ml) were taken and added to 1.5 ml of buffer (pH 9.8) and 1.5 ml of ethyl acetate. After 5 min. of vigorous shaking, a sample (1 ml) of the ethyl acetate layer was taken and the extinction measured at 485 nm.

Figure 3:
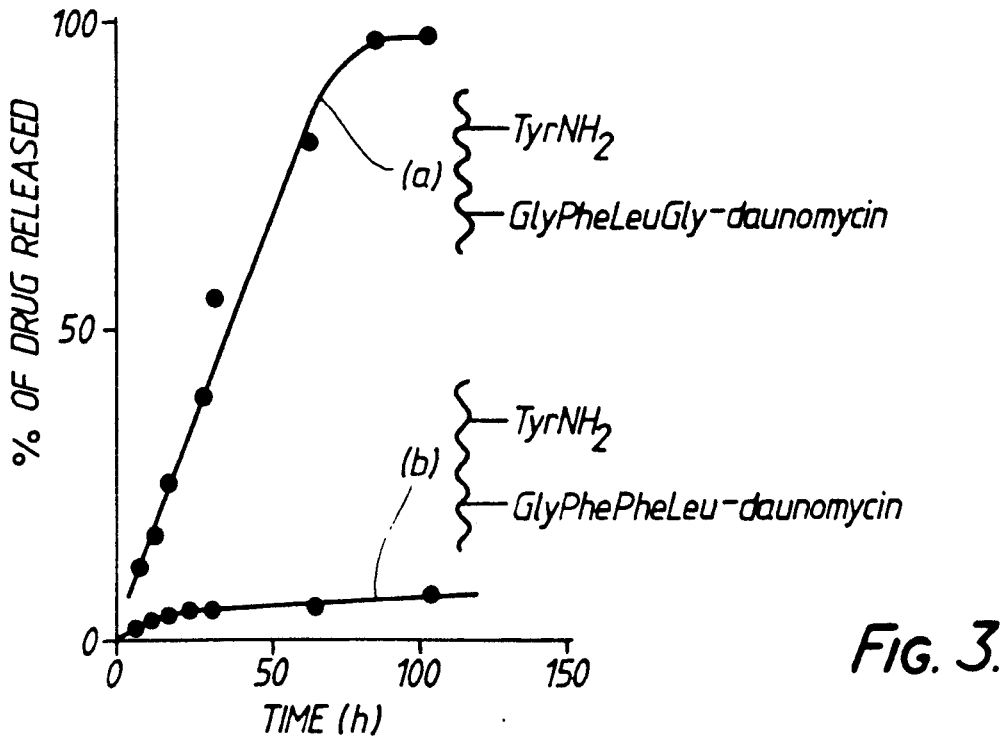
FIG. 3 is a graphical depiction of the percentage of drug released versus time, showing the rate of in vitro drug release in the presence of cathepsin L, as description in Example 25.

The results are shown graphically in FIG. 3 of the accompanying drawings, in which the curves were obtained by plotting the percentage of drug originally present in the analogue which had been released against time in hours. The results indicate that the rate of release of daunomycin is substantially greater when the peptide spacer to the drug is -GlyPheLeuGly- than when it is -GlyPhePheLeu-.

EXAMPLE 26 TO 28

EFFECTS OF DIFFERENT DRUGS HAVING SAME PEPTIDE SPACERS

EXAMPLE 26

(Effect on Activity of L1210 Mouse Leukaemia in vitro)

These experiments were carried out with four HPMA analogues which did not contain determinants; all compounds were of the single chain type and each contained a different drug. The drug spacers of all four compounds were in accordance with the invention; two had -GlyPheLeuGly-spacers and two had -GlyLeuPhe-spacers. In detail, the analogues were as follows,
(a) HPMA with -GlyPheLeuGly-daunomycin and tyrosinamide substituents;
(b) HPMA with -GlyPheLeuGly-puromycin and tyrosinamide substituents;
(c) HPMA with -GlyLeuPhe-sarcolysine substituents; and
(d) HPMA with -GlyLeuPhe-tritylcysteine substituents.

The experimental procedure was the same as that described in Example 22.

Figure 4:
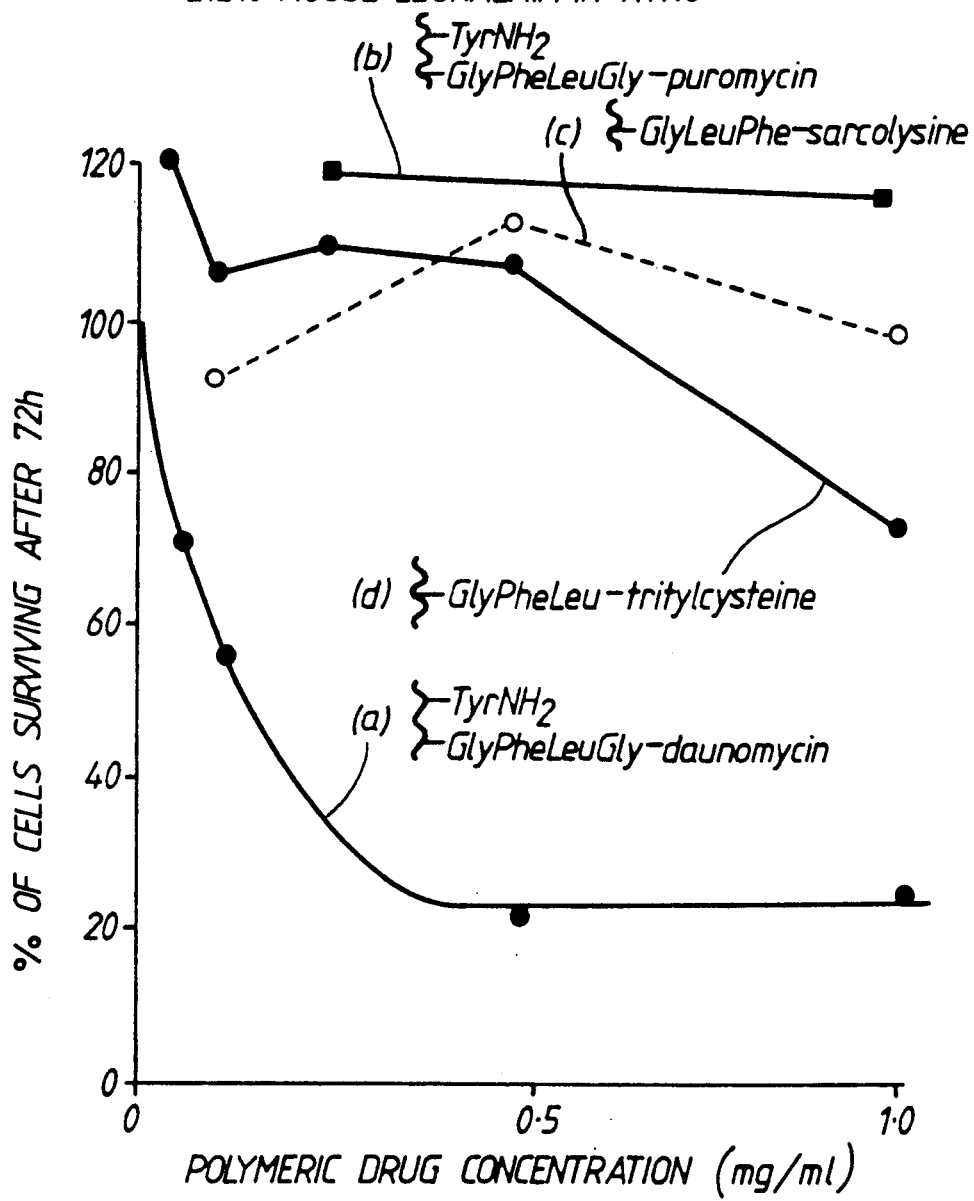
FIG. 4 is a graphical depiction of the percentage of cells surviving after 72 hours versus polymeric drug concentration, showing the effect of various HPMA copolymers on the activity of L1210 mouse leukaemia in vitro, as described in Example 26.

The results are shown graphically in FIG. 4 of the accompanying drawings, in which the curves were obtained by plotting the percentage of cells surviving after 72 hours against the polymeric drug concentration in mg/ml. The results indicate that all four polymeric drugs were cytotoxic to the L1210 leukaemia in vitro to some degree, but with the peptide linkage used daunomycin was considerably more effective than puromycin, and tritylcysteine was slightly more effective than sarcolysine.

EXAMPLE 27

(Effect on Activity of L1210 Mouse Leukaemia in vitro)

Two HPMA analogues were prepared which did not contain determinants. The analogues contained different drugs, but the drug spacer was the same in both cases and was in accordance with the invention. In detail, the analogues were as follows:
(a) HPMA with -GlyGly-deacetylcolchicine substituents, and
(b) HPMA with -GlyGly-colcemid substituents.

The experimental procedure was the same as that described in Example 22.

Figure 5:
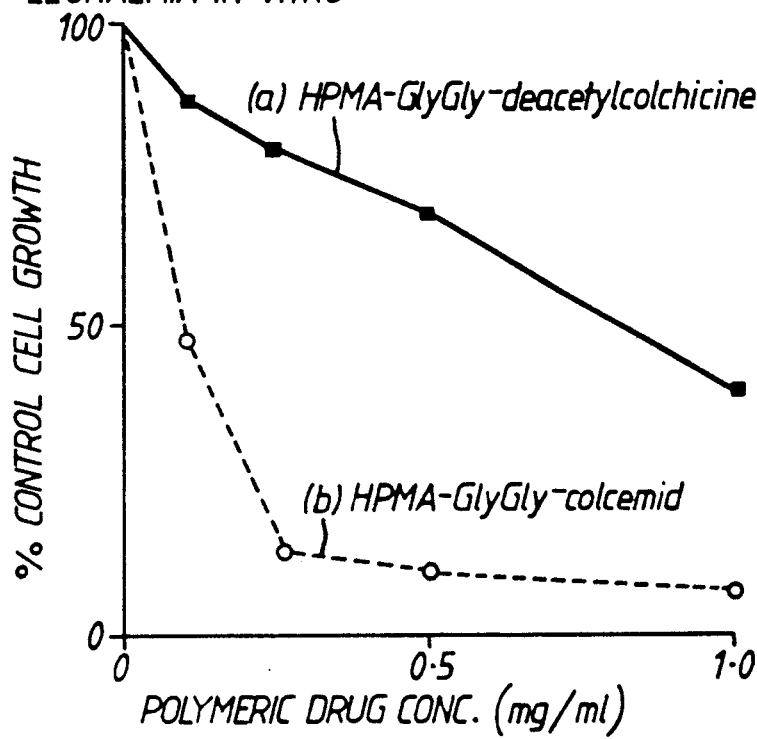
FIG. 5 is a graphical depiction of the percent of control cell growth versus polymeric drug concentration showing the effect of various HPMA copolymers on the activity of L1210 mouse leukaemia in vitro, as described in Example 27.

The results are shown graphically in FIG. 5 of the accompanying drawings, in which the curves were obtained by plotting percentage cell growth against the polymeric drug concentration in mg/ml. The results indicate that both analogues were cytotoxic to L1210 mouse leukaemia in vitro, but analogue (b) had a greater inhibitory effect than analogue (a).

EXAMPLE 28

(Effect on Rate of in vitro Release of Drug in Presence of Enzymes)

Two HPMA analogues were prepared which were of the single chain type and did not contain determinants. The analogues contained different drugs, but the drug spacer was the same in both cases and was in accordance with the invention. In detail, the analogues were as follows:

(a) HPMA with -GlyPheLeuGly-daunomycin and tyrosinamide substituents, and
(b) HPMA with -GlyPheLeuGly-puromycin and tyrosinamide substituents.

Both compounds were examined using two different enzyme solutions, viz. (1) a mixture of isolated rat liver lysosomal enzymes prepared according to the method of Trouet et al (1974) in buffer (pH 5.5) containing 1 mM EDTA, 5 mM reduced glutathione and 0.2% Triton X-100 and, (2) a purified lysosomal enzyme, cathepsin L ($3.8 \times 10^{-7}$ mol/l), in phosphate buffer (pH 6.0) containing 5 mM glutathione and 1 mM EDTA.

Each analogue (25 mg in 1.5 ml) was incubated with 1 ml of the enzyme solution. At various time intervals release of drug was measured by extracting free drug and measuring absorbance at the appropriate wavelength spectrophotometrically. Samples of the incubation mixture (0.15 ml) were taken and added to 1.5 ml of buffer (pH 9.8) and 1.5 ml of ethyl acetate. After 5 min. of vigorous shaking, a sample (1 ml) of the ethyl acetate layer was taken and the extinction measured at 485 nm, in the case of daunomycin, or 272 nm in the case of puromycin.

Figure 6:
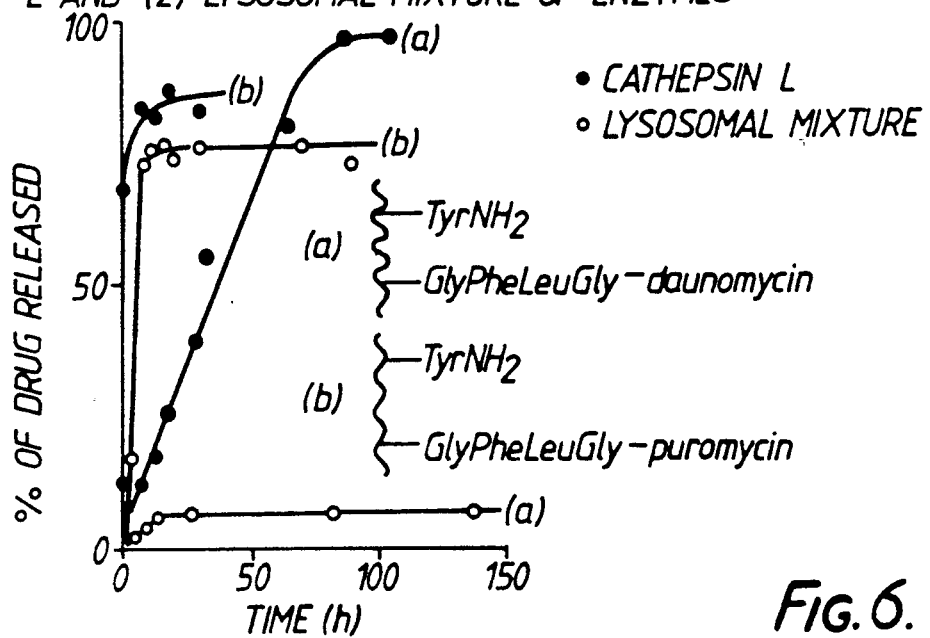
FIG. 6 is a graphical depiction of the rate of in vitro drug release in the presence of (1) cathepsin L and (2) a lysosomal mixture of enzymes, as described in Example 28.

The results are shown graphically in FIG. 6 of the accompanying drawings, in which the curves were obtained by plotting the percentage of drug originally present in the analogue which had been released against time in hours. The results obtained with (1) the mixture of lysosomal enzymes are shown by the open circles, and those obtained with (2) the purified enzyme cathepsin L by the blocked-in circles.

These results show:
(a) differences in the rate of release of puromycin and daunomycin having the same peptide spacer, and
(b) differences in the ability of a purified lysosomal enzyme and a mixture of lysosomal enzymes derived from different sources to degrade the same peptide spacer having the same terminal drug.

[Trouet, A. (1974) *Methods in Enzymology*, (Fleisher, S. and Packer, L., Eds), Vol. XXXI, pp 323–329, Academic Press, New York. EDTA=ethylenediaminetetraacetic acid Triton X-100=quaternary ammonium surfactant.]

EXAMPLES 29 TO 34

EFFECTS OF PRESENCE OF DETERMINANT

EXAMPLE 29

(Effect on Rate of Uptake of Polymer by Melanoma Cells in vitro)

An HPMA analogue containing melanocyte-stimulating hormone (MSH) as the determinant was prepared from α-melanocyte-stimulating hormone; the peptide spacer to the determinant was -GlyGly-, a determinant spacer in accordance with the invention. The analogue was of the cross-linked type (through the MSH) and did not contain a bioactive moiety. A preparation of the analogue was $^{125}$I-radiolabelled and its ability to bind to Clone M3 591 mouse melanoma cells was compared with that of an HPMA control polymer containing tyrosinamide substituents and no determinant substituents. Triplicate cultures were seeded with $2 \times 10^6$ cells and incubated for three days prior to experimentation. 100 μl of each polymer was added to the cultures and incubated for up to 60 minutes. At intervals cultures were terminated and the medium sampled; total cell number and cell associated radioactivity were determined.

The results are shown graphically in FIG. 7 of the accompanying drawings, in which the curves were obtained by plotting uptake in μl of medium/mg of cell protein against time in minutes. The results indicate that the MSH-containing analogue showed increased binding to the melanoma cells compared with the control polymer.

EXAMPLE 30

(Effect on Rate of Uptake of Polymer by Human Fibroblasts in vitro)

An HPMA analogue containing apotransferrin (75 μl, 580 μg/ml) was radiolabelled by the iodogen method; the peptide spacer to the determinant was -GlyGly-, a determinant spacer in accordance with the invention. The compound did not contain a bioactive moiety. Chromatography indicated that the analogue had a molecular weight of about 260.000, corresponding to a formula of polymer (apotransferrin)$_3$.

On the fourth day after subculturing (cells confluent), fibroblast cells (human skin) were washed and incubated for predetermined times in Hank's Balanced Salt solution (3 ml) containing the radiolabelled analogue (200 μl, 11 μg/ml). Samples (1 ml) of medium were counted; cell counts were determined in two separate groups to distinguish between binding and internalisation. Group 1 were trypsinised to remove the ligand binding to the transferrin receptor; group 2 were not given this treatment. Both groups were dissolved in aqueous NaOH and quantified for radioactivity and protein. The rate of uptake was compared with that of an HPMA control polymer containing -GlyPhePheLeu- aminopropanol substituents and no determinant substituents.

The results are shown graphically in FIG. 8 of the accompanying drawings, in which the curves were obtained by plotting uptake in μl of medium/mg of cell protein against time in hours. The results indicate that the apotransferrin-containing polymer showed increased internalisation and binding/internalisation with respect to human fibroblasts as compared with the control polymer.

EXAMPLE 31

(Effect on Uptake of Polymer by Human Hepatoma in vitro)

A series of HPMA analogues containing galactose as the determinant were prepared in which the galactose was bound directly to the polymer backbone via an ester linkage. The analogues contained increasing amounts of galactose varying from 0 to 99 mol %; no bioactive moieties were present. The analogues were labelled with $^{125}$I by the Chloramine T method and tested for their ability to bind to human hepatoma (Hep G2) cells in vitro. The cells were grown as monolayer cultures in EMEM supplemented with 10% foetal bovine serum. Triplicate cultures were seeded with $2 \times 10^6$ cells and then incubated for 3 days before experimentation. The cells were incubated with each analogue (100 μl) for 15 seconds, after which time the medium was sampled and the cell monolayer thoroughly washed. 2.5 ml of 1M NaOH was added to dissolve the cells and samples were taken to determine radiolabel content and total protein.

Figure 9:
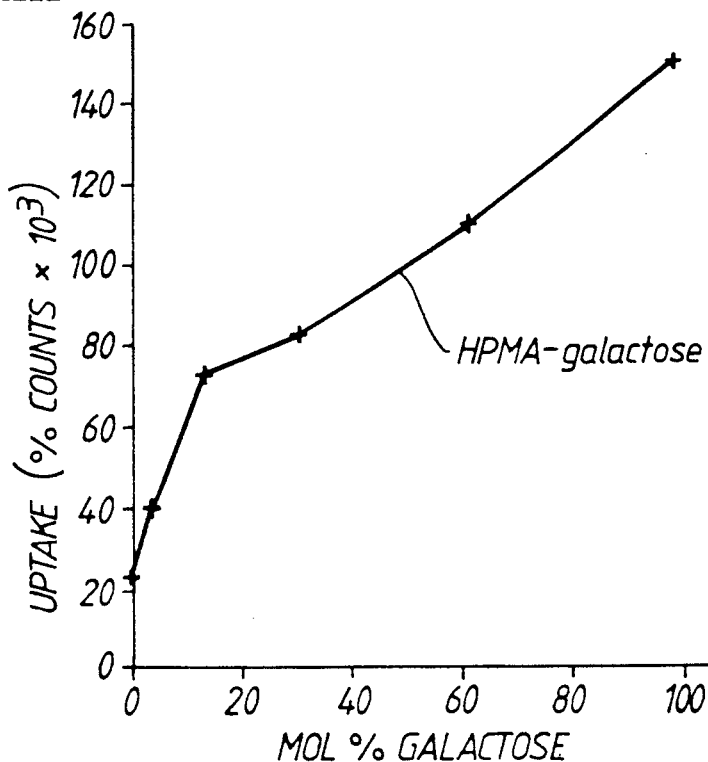
FIG. 9 is a graphical depiction of in vitro uptake of HPMA-galactose copolymer by human hepatoma cells as a function of mol % galactose in a copolymer, as described in Example 31.

The results are shown graphically in FIG. 9 of the accompanying drawings, in which the curves were obtained by plotting uptake in % counts $\times 10^3$/mg of cell protein against mol % of galactose in each analogue. The results indicate that the uptake of HPMA-galactose copolymers by human hepatoma is proportional to the mol % of galactose present.

EXAMPLE 32

(Effect on Activity of L1210 Mouse Leukaemia in vitro)

These experiments were carried out with two HPMA copolymers, one of which was in accordance with the invention. Both compounds contained daunomycin as the bioactive moiety and -GlyPheLeuGly- as the drug spacer. The compound in accordance with the invention further contained fucosylamine as a determinant and -GlyPheLeuGly-as the determinant spacer.

The experimental procedure was the same as that described in Example 22.

Figure 10:
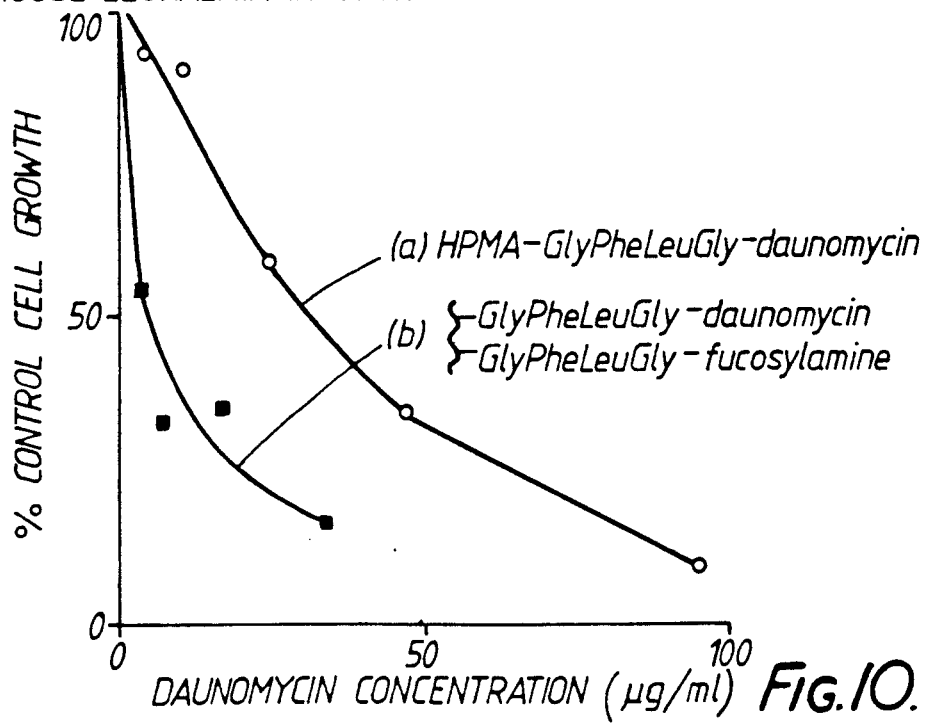
FIG. 10 is a graphical depiction of the percentage of control cell growth versus daunomycin concentration, showing the effect of HPMA-daunomycin copolymers on the activity of L1210 mouse leukaemia in vitro, as described in Example 32.

The results are shown graphically in FIG. 10 of the accompanying drawings, in which the curves were obtained by plotting percentage cell growth against the daunomycin concentration in μg/ml. The results indicate that the cytotoxicity of the polymeric drug to L1210 mouse leukaemia in vitro is significantly increased by the presence of a fucosylamine determinant in the molecule.

EXAMPLE 33

(Effect on in vivo Targeting of Polymer)

Two HPMA copolymers were prepared which had the following structures and compositions:

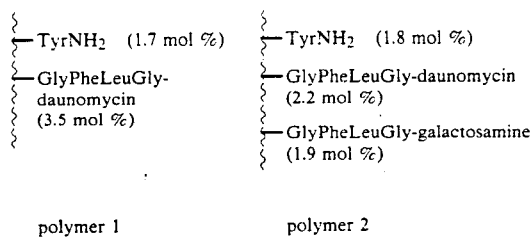

polymer 1    polymer 2

Polymer 2 is in accordance with the invention, polymer 1 is not.

Both HPMA polymers were radiolabelled with $^{125}I$ using the Chloramine T method of iodination. This radiolabel is stable in the biological environment and therefore enables the fate of the polymer to be followed in vivo.

Polymer (approximately 100 μg in 0.1 ml of buffer) was injected into the femoral vein of a male Wistar rat (250–350 g) maintained under anaesthetic and after a thirty minute period the animal was sacrificed and the body distribution of radioactivity measured.

The results obtained are shown in Table 2.

TABLE 2

| Body distribution (after 30 minutes) | Polymer 1 | Polymer 2 |
|---|---|---|
| | % of radioactivity recovered | |
| Spleen | 0.51 | 0.19 |
| Kidneys | 4.39 | 4.83 |
| Lungs | 1.34 | 1.37 |
| Liver | 4.97 | 23.20 |
| Blood | 88.77 | 70.38 |

It can be seen from these results that inclusion of even a small amount of galactosamine (1.9 mol %) effectively diverts a substantial amount of HPMA copolymer to the rat liver within 30 minutes of intravenous administration.

EXAMPLE 34

(Effect on Activity of L1210 Mouse Leukaemia in vivo)

These experiments were carried out with two HPMA analogues, one of which was in accordance with the invention. Both analogues contained daunomycin as the bioactive moiety, -GlyPheLeuGly-as the drug spacer, and tyrosinamide residues. The polymer in accordance with the invention also contained fucose as a determinant; the spacer to the determinant was -GlyPheLeuGly-. In detail, the polymers were as follows:

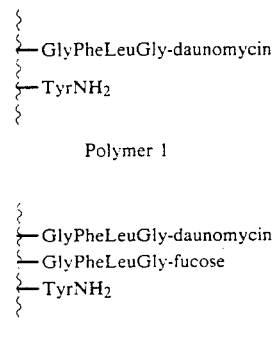

The mouse leukaemia L1210 was inoculated ($10^5$ viable cells) intraperitoneally into $DBA_2$ mice on day 0. The animals were then divided into two groups which were treated separately. The animals of group 1 were treated with polymer 1 and the animals of group 2 were treated with Polymer 2; in both groups the dose administered was equivalent to 7.5 mg of daunomycin/kg. Survival of the animals in both groups was monitored.

The results showed that the survival rate of the animals in group 2 (copolymer in accordance with the invention) was at least double the survival rate of the animals in group 1 (no determinant in copolymer); thus, in one set of experiments, the long term survival rate in group 2 was 57% compared with a long term survival rate in group 1 of only 25%.

EXAMPLE 35

Effect of Different Peptide Spacers to Same Determinant/Drug on in vivo Targeting of Polymer These experiments were carried out with two HPMA copolymers, both of which were in accordance with the invention. The copolymers both contained daunomycin as the bioactive moiety and an anti-θ antibody as the determinant. The peptide spacer to the drug and the determinant was the same for each copolymer but different in the two compounds. In detail, the copolymers were as follows:

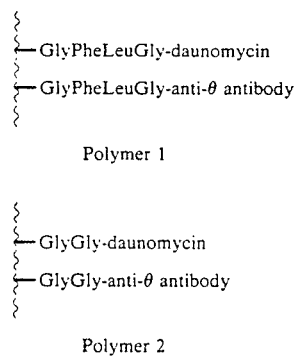

Polymer 1

Polymer 2

The activity of the copolymers was tested against T-lymphocytes in vivo by measuring the suppression of anti-sheep red blood cell response in mice. The results obtained are shown in Table 3.

TABLE 3

|  | Polymer 1 | Polymer 2 |
|---|---|---|
| Total dose per mouse of anti-Θ antibody (mg) | 3.0 | 3.0 |
| Total dose per mouse of daunomycin (mg) | 0.4 | 0.6 |
| % suppression of immune response | 98 | 0 |

It can be seen from these results that polymer 1 containing -GlyPheLeuGly- spacers to the drug and determinant is considerably more effective in killing T-lymphocytes than the corresponding polymer (2) containing -GlyGly-spacers.

We claim:

1. A drug conjugate comprising an inert synthetic polymeric carrier combined through peptide spacers with a bioactive molecule, with a targeting moiety, and with an optional cross-linkage, which comprises
   (a) 5.0 to 99.7 mol % of units derived from N-(2-hydroxypropyl)methacrylamide;
   (b) 0.2 to 20.0 mol % of units derived from an N-methacryloylated peptide, the peptide being covalently bound to a bioactive molecule and also being subject to intracellular lysosomal hydrolysis, said peptide being selected from Gly-Gly, Gly-Phe-Gly, Gly-Phe-Phe, Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, and Gly-Gly-Phe-Leu-Gly-Phe;
   (c) 0.1 to 94.8 mol % of units derived from N-methacrylamide, N-methacrylic acid or an N-methacryloylated amino acid or peptide, to which are covalently bound a targeting moiety which is a determinant capable of interacting with specific receptors on cell surfaces, the amino acid or peptide being selected from Leu, Phe, Gly-Gly, Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, and Gly-Gly-Phe-Leu-Gly-Phe;
   (d) optionally, 0 to 5 mol % of units derived from an N-methacryloylated peptide, the peptide groups being covalently bound to a linking group which is covalently attached to a similar peptide group attached to another polymer chain, the peptide being selected from Gly-Leu-Gly, Gly-Val-Ala, Gly-Phe-Ala, Gly-Leu-Phe, Gly-Leu-Ala, Ala-Val-Ala, Gly-Phe-Leu-Gly, Gly-Phe-Phe-Leu, Gly-Leu-Leu-Gly, Gly-Phe-Tyr-Ala, Gly-Phe-Gly-Phe, Ala-Gly-Val-Phe, Gly-Phe-Phe-Gly, Gly-Phe-Leu-Gly-Phe, and Gly-Gly-Phe-Leu-Gly-Phe; and
   (e) optionally, as a bioassay label, 0 to 2 mol % of units derived from N-methacryloylated tyrosinamide.

2. The drug conjugate according to claim 1 wherein the determinant is a monosaccharide, disaccharide or oligosaccharide bound by an amide linkage, an antibody or a protein.

3. The drug conjugate according to claim 2 wherein the saccharide determinant is galactose, galactosamine, gluosamine, mannosamine or fucosylamine.

4. The drug conjugate according to claim 1 wherein the determinant is IgG or anti-θ antibody.

5. The drug conjugate according to claim 1 wherein the bioactive molecule is an anti-cancer agent, an antimicrobial agent, an antiparasitic agent, an anti-inflammatory agent, a cardio-vascular drug, or a drug acting on the nervous system.

6. The drug conjugate according to claim 1 wherein the bioactive molecule is daunomycin, puromycin, adriamycin, melphalan isopropyl ester (sarcolysine), bleomycin, desferioxamine, bestatin, or tritylcysteine.

7. The drug conjugate according to claim 1 wherein the linking group of (d) is present and is of the type -(amino acid)—NH(CH$_2$)$_x$NH—(amino acid)-, where x is an integer of from 1 to 12, and which is attached to adjacent peptide groups by amide linkages.

8. The drug conjugate according to claim 7 wherein x is 6 and the amino acid is Phe, Tyr, Ala, Gly, or Leu.

9. The drug conjugate according to claim 7 wherein x is 2 and the amino acid is Ala.

10. The drug conjugate according to claim 1 wherein the bioactive molecule is daunomycin, and the determinant is galactose, galactosamine or fucosylamine.

11. The drug conjugate according to claim 10 cross-linked with a cross-linking spacer comprising Gly-Phe-Leu-Gly and the linking group comprises -(Phe)NH(CH$_2$)$_6$NH(Phe)-.

12. The process for the synthesis of a drug conjugate according to claim 1 which comprises copolymerizing N-(2-hydroxypropyl)methacrylamide with either an N-methacryloylated amino acid or peptide or the p-nitrophenyl ester thereof, and reacting the resultant copolymer with a reactive bioactive molecule and a reactive determinant.

13. The process according to claim 12 wherein N-methacryloylated tryosinamide is included in the copolymerization step as a bioassay label.

14. The process according to claim 12 wherein a diamine cross-linking agent is included in the reaction between the resultant copolymer, the reactive bioactive molecule and the reactive determinant.

15. The process according to claim 12 wherein a diamine cross-linking agent is included in the reaction between the resultant copolymer and the reactive bioactive molecule.

16. The process for the synthesis of a drug conjugate according to claim 1 which comprises copolymerizing N-(2-hydroxypropyl)methacrylamide an N-methacryloylated determinant or N-methacryloylated amino acid or peptidyl determinant, and either an N-methacryloylated peptide or the p-nitrophenyl ester thereof, and reacting the resultant copolymer with a reactive bioactive molecule.

17. The process according to claim 16 wherein N-methacryloylated tryosinamide is included in the copolymerization step as a bioassay label.

18. A pharmaceutical composition comprising at least one drug conjugate according to claim 11 and an inert, physiologically acceptable carrier.

19. The pharmaceutical composition according to claim 18 wherein the carrier is a sterile aqueous medium and the composition is formulated for injection.

* * * * *

UNITED STATES PATENT AND TRADEMARK OFFICE
CERTIFICATE OF CORRECTION

PATENT NO. : 5,037,883
DATED : August 6, 1991
INVENTOR(S) : Jindrich Kopecek, et al.

It is certified that error appears in the above-identified patent and that said Letters Patent is hereby corrected as shown below:

On Title Page:

Correct the name of the second named assignee by deleting "Carlton Medical Products Limited" and substituting therefor --Cancer Research Campaign Technology Limited--.

Following the filing date, insert the following:

--Related U.S. Application Data

[62] Continuation of Ser. No. 816,138, Jan. 3, 1986, abandoned.--

Signed and Sealed this

Thirteenth Day of October, 1992

Attest:

DOUGLAS B. COMER

Attesting Officer

Acting Commissioner of Patents and Trademarks